United States Patent
Perros et al.

(10) Patent No.: US 6,667,314 B2
(45) Date of Patent: Dec. 23, 2003

(54) TROPANE DERIVATIVES USEFUL IN THERAPY

(75) Inventors: Manoussos Perros, County of Kent (GB); David Anthony Price, County of Kent (GB); Blanda Luzia Christa Stammen, County of Kent (GB); Anthony Wood, County of Kent (GB)

(73) Assignee: Pfizer, Inc., New York, NY (US)

( * ) Notice: Subject to any disclaimer, the term of this patent is extended or adjusted under 35 U.S.C. 154(b) by 0 days.

(21) Appl. No.: 09/865,950

(22) Filed: May 25, 2001

(65) Prior Publication Data

US 2002/0013337 A1 Jan. 31, 2002

Related U.S. Application Data

(60) Provisional application No. 60/214,587, filed on Jun. 27, 2000, and provisional application No. 60/219,202, filed on Jul. 19, 2000.

(30) Foreign Application Priority Data

Jun. 27, 2000 (GB) ................................. 0015835

(51) Int. Cl.$^7$ ................. A61K 31/46; C07D 451/04; A61P 29/00; A61P 31/18
(52) U.S. Cl. ................. 514/304; 546/125; 560/37; 560/38; 564/191
(58) Field of Search ................. 546/125; 514/304; 560/38; 564/191

(56) References Cited

U.S. PATENT DOCUMENTS 5,968,947 A * 10/1999 Urch et al. ................. 514/299
6,586,430 B1 * 7/2003 Armour et al. ........... 514/235.2

FOREIGN PATENT DOCUMENTS

| EP | 0630887 | 12/1994 |
|----|---------|---------|
| EP | 0903349 | 3/1999 |
| WO | 9719060 | 5/1997 |
| WO | 9724325 | 7/1997 |
| WO | 9802151 | 1/1998 |
| WO | 9825604 | 6/1998 |
| WO | 9825617 | 6/1998 |
| WO | 9904794 | 2/1999 |
| WO | 9917773 | 4/1999 |
| WO | 9937617 | 7/1999 |
| WO | 9937619 | 7/1999 |
| WO | 0038680 | 7/2000 |

OTHER PUBLICATIONS

Hesselgesser J et al. (1998) J. Biol. Chem. 273(25), 15687–15692.*

* cited by examiner

Primary Examiner—Evelyn Mei Huang
(74) Attorney, Agent, or Firm—Peter Richardson; Bryan C. Zielinski; Keith D. Hutchinson

(57) ABSTRACT

The present invention provides compounds of the formula:

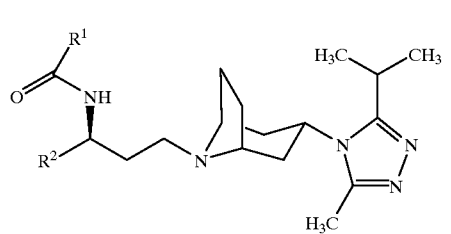

wherein $R^1$ is $C_{3-6}$ cycloalkyl optionally substituted by one or more fluorine atoms, or $C_{1-6}$ alkyl optionally substituted by one or more fluorine atoms, or $C_{3-6}$ cycloalkylmethyl optionally ring-substituted by one or more fluorine atoms; and $R^2$ is phenyl optionally substituted by one or more fluorine atoms, to pharmaceutically acceptable salts and solvates thereof, and to processes for the preparation of, intermediates used in the preparation of, compositions containing and the uses of, such compounds.

35 Claims, No Drawings

TROPANE DERIVATIVES USEFUL IN THERAPY

CROSS REFERENCE TO RELATED APPLICATIONS

This application claims the benefit of priority of foreign application numbers GB 0014046.7 and GB 0015835.2, filed in Great Britain on May 26, 2000 and Jun. 27, 2000, respectively. This application also claims the benefit of priority of U.S. Provisional Application Nos. 60/214,587 and 60/219,202, filed Jun. 27, 2000 and Jul. 19, 2000, respectively.

This invention relates to tropane derivatives useful in the treatment of a variety of disorders, including those in which the modulation of CCR5 receptors is implicated. More particularly, the present invention relates to 3-(3-isopropyl-5-methyl-4H-1,2,4-triazol-4-yl)-exo-8-azabicyclo[3.2.1] octane derivatives and to processes for the preparation of, intermediates used in the preparation of, compositions containing and the uses of, such derivatives. Disorders that may be treated or prevented by the present derivatives include HIV and genetically related retroviral infections (and the resulting acquired immune deficiency syndrome, AIDS), and inflammatory diseases.

The compounds of the present invention are modulators, especially antagonists, of the activity of chemokine CCR5 receptors. Modulators of the CCR5 receptor may be useful in the treatment of various inflammatory diseases and conditions, and in the treatment of infection by HIV-1 and genetically related retroviruses. The name "chemokine", is a contraction of "chemotactic cytokines". The chemokines comprise a large family of proteins which have in common important structural features and which have the ability to attract leukocytes. As leukocyte chemotactic factors, chemokines play an indispensable role in the attraction of leukocytes to various tissues of the body, a process which is essential for both inflammation and the body's response to infection. Because chemokines and their receptors are central to the pathophysiology of inflammatory and infectious diseases, agents which are active in modulating, preferably antagonizing, the activity of chemokines and their receptors, are useful in the therapeutic treatment of such inflammatory and infectious diseases.

The chemokine receptor CCR5 is of particular importance in the context of treating inflammatory and infectious diseases. CCR5 is a receptor for chemokines, especially for the macrophage inflammatory proteins (MIP) designated MIP-1α and MIP-1β, and for a protein which is regulated upon activation and is normal T-cell expressed and secreted (RANTES).

There has been a substantial investigation of different classes of modulators of chemokine receptor activity, especially that of the CCR5 chemokine receptor, for example, WO 98/25617 relates to substituted aryl piperazines as modulators of chemokine receptor activity.

The present compounds are generally disclosed by WO 00/38680 but none is specifically exemplified therein.

According to a first aspect of the present invention, there is provided a compound of formula (I),

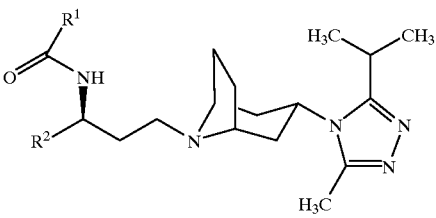

wherein $R^1$ is $C_{3-6}$ cycloalkyl optionally substituted by one or more fluorine atoms, or $C_{1-6}$ alkyl optionally substituted by one or more fluorine atoms, or $C_{3-6}$ cycloalkylmethyl optionally ring-substituted by one or more fluorine atoms; and $R^2$ is phenyl optionally substituted by one or more fluorine atoms:

or a pharmaceutically acceptable salt or solvate thereof.

According to a second aspect of the present invention, there is provided a compound of formula (IA),

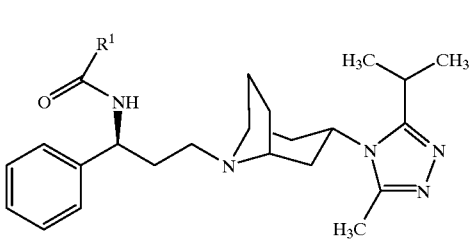

wherein $R^1$ represents either $C_{3-6}$ cycloalkyl optionally substituted by one or more fluorine atoms, or $C_{1-6}$ alkyl optionally substituted by one or more fluorine atoms, or a pharmaceutically acceptable salt or solvate thereof.

"$C_{1-6}$ alkyl" in the definition of $R^1$ includes straight-chain and branched groups. Examples of alkyl include methyl, ethyl, n-propyl, i-propyl, n-butyl, i-butyl, sec-butyl and t-butyl. "$C_{3-6}$ cycloalkyl" means cyclopropyl, cyclobutyl, cyclopentyl and cyclohexyl.

The compounds of formula (I) contain a basic centre and suitable acid addition salts are formed from acids which form non-toxic salts. Examples include the hydrochloride, hydrobromide, hydroiodide, sulphate, bisulphate, nitrate, phosphate, hydrogen phosphate, acetate, maleate, fumarate, lactate, tartrate, citrate, gluconate, camsylate, succinate, saccharate, benzoate, methanesulphonate, ethanesulphonate, benzenesulphonate, p-toluenesulphonate and pamoate salts. For a review on suitable salts see Berge et al, J. Pharm. Sci., 66, 1–19, 1977.

The pharmaceutically acceptable solvates of the compounds of the formula (I) or salts thereof include the hydrates thereof.

Also included within the present scope of the compounds of the formula (I) are polymorphs thereof.

A compound of the formula (I) contains one or more asymmetric carbon atoms and therefore exists in two or more stereoisomeric forms. The present invention includes the individual stereoisomers of the compounds of the formula (I) and, where appropriate, the individual tautomeric forms thereof, together with mixtures thereof.

Separation of diastereoisomers may be achieved by conventional techniques, e.g. by fractional crystallisation, chromatography or H.P.L.C. of a stereoisomeric mixture of a compound of the formula (I) or a suitable salt or derivative thereof. An individual enantiomer of a compound of the formula (I) may also be prepared from a corresponding optically pure intermediate or by resolution, such as by H.P.L.C. of the corresponding racemate using a suitable chiral support or by fractional crystallisation of the diastereoisomeric salts formed by; reaction of the corresponding racemate with a suitable optically active acid or base, as appropriate.

The invention also includes isotopically labelled compounds of the formula (I).

Preferably, $R^1$ is either $C_{4-6}$ cycloalkyl optionally substituted by one or two fluorine atoms, or $C_{1-4}$ alkyl optionally substituted by from one to three fluorine atoms.

Preferably, $R^1$ is either cyclobutyl, cyclopentyl, 4,4-difluorocyclohexyl or 3,3,3-trifluoropropyl.

Preferably, $R^2$ is phenyl optionally substituted by 1 or 2 fluorine atom(s).

Preferably, $R^2$ is phenyl or monofluorophenyl.

Preferably, $R^2$ is phenyl or 3-fluorophenyl.

Preferred compounds of the formula (I) include

N-{(1S)-3-[3-(3-Isopropyl-5-methyl-4H-1,2,4-triazol-4-yl)-exo-8-azabicyclo[3.2.1]oct-8-yl]-1-phenylpropyl}cyclobutanecarboxamide;

N-{(1S)-3-[3-(3-Isopropyl-5-methyl-4H-1,2,4-triazol-4-yl)-exo-8-azabicyclo[3.2.1]oct-8-yl]-1-phenylpropyl}cyclopentanecarboxamide;

N-{(1S)-3-[3-(3-Isopropyl-5-methyl-4H-1,2,4-triazol-4-yl)-exo-8-azabicyclo[3.2.1]oct-8-yl]-1-phenylpropyl}-4,4,4-trifluorobutanamide;

N-{(1S)-3-[3-(3-Isopropyl-5-methyl-4H-1,2,4-triazol-4-yl)-exo-8-azabicyclo[3.2.1]oct-8-yl]-1-phenylpropyl}-4,4-difluorocyclohexanecarboxamide; and N-{(1S)-3-[3-(3-Isopropyl-5-methyl-4H-1,2,4-triazol-4-yl)-exo-8-azabicyclo[3.2.1]oct-8-yl]-1-(3-fluorophenyl)propyl}-4,4-difluorocyclohexanecarboxamide: or a pharmaceutically acceptable salt or solvate of any thereof.

The compounds of the formula (I) may be prepared by the following general methods in which $R^1$ and $R^2$ are as previously defined for a compound of the formula (I) unless otherwise stated.

1. A compound of the formula (I) may be prepared by reacting a compound of formula:

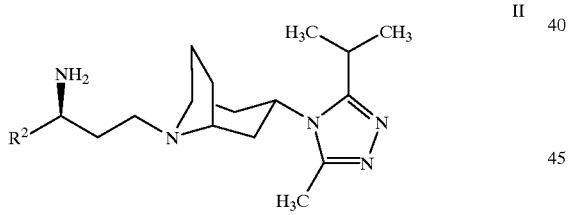

(II)

with a compound of formula:

$R^1CO_2H$ (III)

under conventional coupling conditions.

The reaction is preferably carried out in the presence of a suitable coupling agent (for example, N-benzyl-N'-cyclohexylcarbodiimide (which may be polymer-bound), or hydroxybenzotriazole hydrate and 1-(3-dimethylaminopropyl)-3-ethylcarbodiimide methiodide), at about room temperature, in a solvent that does not adversely affect the reaction, for example, dichloromethane. Further suitable coupling conditions are described in Method 2 below.

The compounds of formula (III) are either known or are prepared using conventional techniques.

The compounds of the formula (II) may be prepared as shown in Scheme 1 below.

2. The compounds of the formula (I) may be prepared as shown in Scheme 1.

Scheme 1

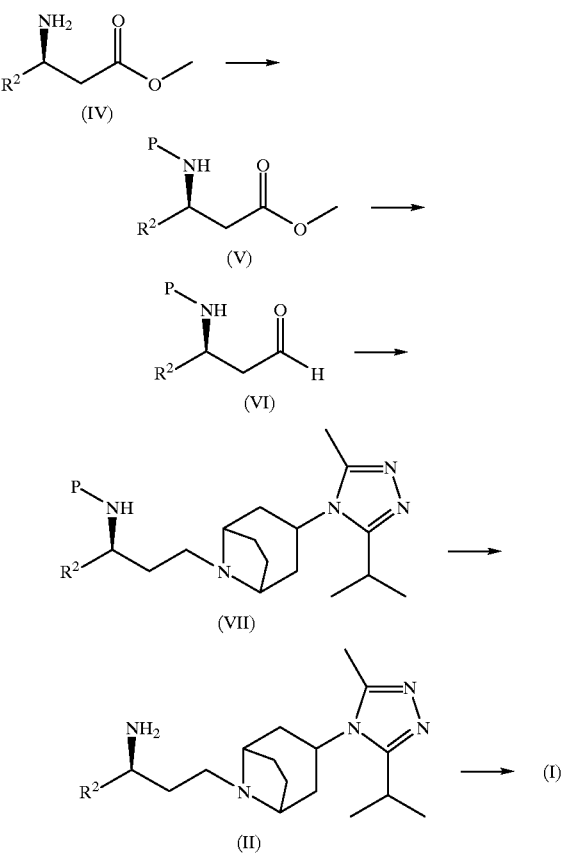

wherein P is a suitable protecting group such as t-butyloxycarbonyl, benzyl or benzyloxycarbonyl and the compounds of the formula (II) and (VII) are in the exo form. In a typical procedure, where P is t-butyloxycarbonyl, an amine of the formula (IV) is reacted with di-tert-butyl dicarbonate in the presence of a base acceptor such as aqueous sodium hydroxide and in a suitable solvent such as tetrahydrofuran.

The protected amine of the formula (V) may be reduced to an aldehyde of the formula (VI) using a suitable reducing agent, e.g., using diisobutylaluminium hydride in dichloromethane at below −70° C.

Reductive amination reaction of the aldehyde of the formula (VI) with an amine of the formula (in the exo form):

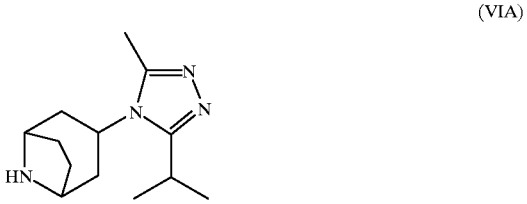

(VIA)

leads to a compound of the formula (VII). The reaction may be carried out in the presence of an excess of a suitable reducing agent, e.g. sodium triacetoxyborohydride or sodium cyanoborohydride, in a protic solvent system e.g., acetic acid in either dichloromethane or 1,1,1-trichloroethane, at room temperature.

Deprotection of a compound of the formula (VII) may be accomplished using conventional conditions. Where P is t-butyloxycarbonyl this may be achieved using trifluoroacetic acid or aqueous hydrochloric acid in a solvent such as dichloromethane or methanol at room temperature.

A compound of the formula (II) prepared may be converted to a compound of the formula (I) by reaction with a compound of the formula:

R$^1$COZ (VIB)

wherein Z is a carboxylic acid activating group such as chloro or 1H-imidazol-1-yl, using conventional conditions, e.g. using N,N'-carbonyldiimidazole, triethylamine and dichloromethane.

Preferably, a compound of the formula (VIB) is generated in situ from a compound of the formula (III) using a carbodiimide such as 3-(3-dimethylamino-1-propyl)-1-ethylcarbodiimide or N-benzyl-N'-cyclohexylcarbodiimide-polymer bound, optionally in the presence of 1-hydroxybenzotriazole hydrate, and reacted with a compound of the formula (II). The reaction may be performed in a suitable solvent such as dichloromethane, tetrahydrofuran or ethyl acetate, optionally in the presence of a base such as a tertiary amine, e.g. triethylamine or N-ethyldiisopropylamine, at about room temperature.

Alternatively, the acid of the formula (III) may be first activated with benzotriazol-1-yloxy-tris(dimethylamino)phosphonium hexafluorophosphate (BOP), bromo-tris-pyrrolidinophosphonium hexafluorophosphate (PYBrOP), or 2-fluoro-1-methylpyridinium p-toluenesulphonate (Mukaiyama's reagent) in the presence of an excess of N-methylmorpholine, triethylamine or N-ethyldiisopropylamine in a suitable solvent such as tetrahydrofuran, dichloromethane or ethyl acetate, at room temperature to provide a compound of the formula (VIB) and this is reacted with a compound of the formula (11).

Alternatively, an acid chloride of formula (VIB) wherein Z is chloro may be reacted with a compound of the formula (II), optionally in the presence of a suitable base, e.g. triethylamine, N-ethyldiisopropylamine, sodium carbonate, potassium carbonate or sodium bicarbonate, and in a suitable solvent such as dichloromethane, ethyl acetate, THF or toluene, at room temperature.

It will be appreciated that the transformation of a compound of the formula (VII) to a compound of the formula (I) via a compound of the formula (II) can be performed in a "one-pot procedure" by deprotection/coupling using similar methods to those previously described.

A compound of the formula (VIA) may be prepared as shown in Scheme 2.

Scheme 2

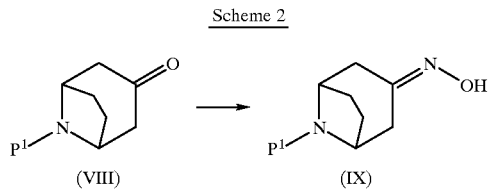

(VIII)      (IX)

-continued

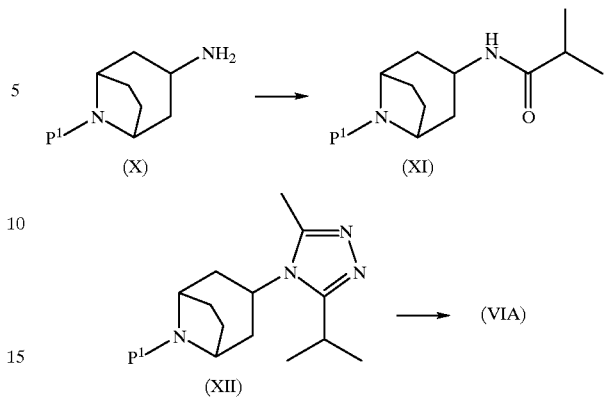

wherein P$^1$ is a suitable protecting group such as t-butyloxycarbonyl or benzyl and the compounds of the formulae (X), (XI) and (XII) are in the exo form.

An oxime of the formula (IX) may be prepared by the condensation of a ketone of the formula (VIII) with hydroxylamine hydrochloride in the presence of a base, e.g. pyridine, and in a suitable solvent, typically ethanol. The reaction is typically carried out at the reflux temperature of the solvent.

Where P$^1$ is t-butyloxycarbonyl or benzyl, reduction of an oxime of the formula (IX) may be achieved using sodium in the presence of an alcohol, typically pentanol, or by electrochemical reduction, to provide an amine of the formula (X).

An amide of the formula (XI) may be prepared by coupling the protected amine of the formula (X) with 2-methylpropanoic acid, or an activated derivative thereof. The coupling may be achieved using conventional amide bond forming techniques, such as as described in Methods 1 and 2 above. Typically, the acid may be first activated using a carbodiimide such as 1-(3-dimethylaminopropyl)-3-ethyl-carbodiimide, optionally in the presence of 1-hydroxybenzotriazole, in a suitable solvent such as dichloromethane, and in the presence of a base, e.g. a tertiary amine such as triethylamine or diisopropylamine, and then reacted with the amine of the formula (X). Alternatively, the reaction may be performed using 2-methylpropanoyl chloride in the presence of a base such as sodium carbonate and a suitable solvent, e.g. dichloromethane.

A triazole of the formula (XII) may be prepared in a "one-pot", two-step procedure by first coupling an amide of the formula (XI) with acetic hydrazide followed by in-situ cyclo-condensation. Typically, the amide is first activated with phosphorous oxychloride in a solvent such as chloroform and in the presence of a base, e.g. pyridine, at 0° C., then treated with acetic hydrazide in a suitable solvent, e.g. chloroform, and the reaction heated under reflux. The reaction may be driven to completion in the presence of an acid, e.g. p-toluenesulphonic acid, and in a suitable solvent such as toluene at elevated temperature (e.g., 110° C.).

Deprotection of the compound of the formula (XII) using standard methodology provides the amine of the formula (VIA). Typically, where P$^1$ is benzyl, deprotection is performed by catalytic hydrogenation such as using palladium (II) hydroxide as the catalyst in a suitable solvent, e.g. ethanol, in the presence of ammonium formate at 70+ C. Alternatively, the deprotection may be performed by catalytic hydrogenation using palladium-on-charcoal as the catalyst in a suitable solvent such as methanol, optionally in the presence of a suitable acid such as p-toluenesulphonic acid.

3. The compounds of the formula (I) may be prepared as shown in Scheme 3.

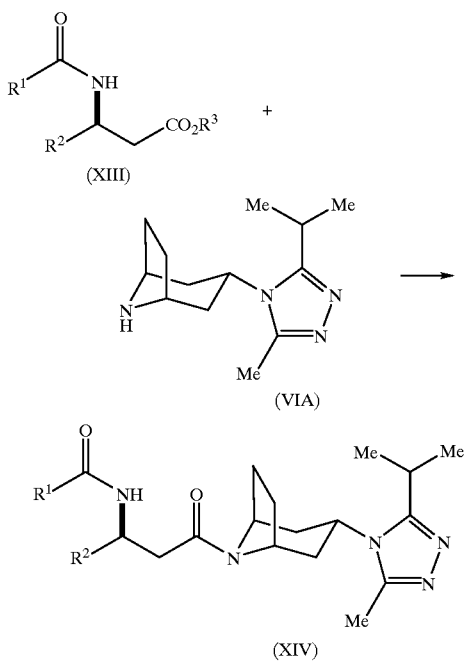

wherein $R^3$ is H or $C_1$–$C_6$ alkyl.

An amide of the formula (XIV) may be formed by conventional amide bond formation techniques such as by first activating an acid of the formula (XIII) (wherein $R_3$ is H) either as an acid chloride or using other procedures as described above in Methods 1 and 2, followed by reaction with the amine of the formula (VIA). Alternatively an ester of the formula (XIII) (wherein $R^3$ is $C_1$–$C_6$ alkyl) may reacted directly with the amine or a metal salt thereof. Thus the acid chloride and the amine, or a salt thereof, may be reacted in the presence of an excess of a; suitable base, e.g. $Na_2CO_3$, $NaHCO_3$, $K_2CO_3$, triethylamine or N,N-diisopropylethylamine, and in a suitable solvent, e.g. dichloromethane, ethyl acetate, THF or toluene, with or without water as a co-solvent. Alternatively the acid may be activated with 1-[3-(dimethylamino)propyl]-3-ethylcarbodiimide hydrochloride (WCDl), CDl (1,1'-carbonyldiimidazole) or DCC (1,3-dicyclohexylcarbodiimide) and HOAT (1-hydroxy-7-azabenzotriazole) or HOBT (1-hydroxybenzotriazole hydrate), and reacted with the amine in the presence of a base, e.g. triethylamine, in a solvent such as THF, dichloromethane or toluene. Also, the ester and the amine or a metal salt thereof, may reacted together in the presence of a base, e.g. triethylamine, and an optional catalyst in a solvent such as dichloromethane, ethyl acetate, THF or toluene, with or without water as co-solvent. Alternatively, the ester, the amine and an enzyme-catalyst may be reacted together in a solvent such as dichloromethane, ethyl acetate, THF or toluene, with or without water as co-solvent. Preferably, the acid chloride, the amine and $Na_2CO_3$ are reacted together in dichloromethane and water, or the acid is treated with N,N'-carbonyldiimidazole to form the imidazolide and then reacted with the amine in dichloromethane in the presence of triethylamine.

The amide of the formula (XIV) may be reduced, such as by using a nucleophilic hydride reagent or an electrophilic hydride reagent, or by catalytic hydrogenation, or by using an alkyl or aryl-silane with a suitable transition metal catalyst, to provide a compound of the formula (I). Typical conditions include using Red-Al® (sodium bis(2-methoxyethoxy)aluminium hydride) in THF or toluene, or borane in THF.

4. The compounds of the formula (I) may be prepared as shown in Scheme 4.

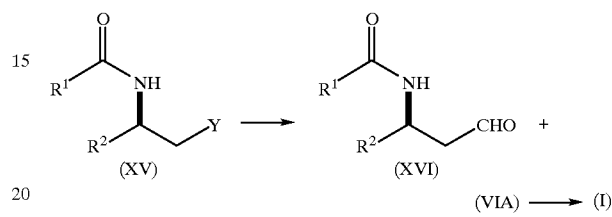

wherein Y is $-CO_2R^4$, $-CN$ or $-C(O)NHR^4$, wherein $R^4$ is H or $C_1$–$C_6$ alkyl The reaction to prepare an aldehyde of the formula (XVI) may be performed by reduction of an ester, nitrile, amide or acid (e.g. activated by a suitable reagent) of the formula (XV), such as with a hydride reducing agent in a suitable solvent. Alternatively, reduction of an ester, nitrile or acid (activated by a suitable reagent) of the formula (XV) may be achieved with a suitable transition metal catalyst, a hydrogen source and in a suitable solvent. Typical conditions include reducing the ester, nitrile or amide with an aluminium or boron hydride such as DIBAL (diisobutylaluminium hydride), Red-Al®, $LiAl(O(t-Bu))_3$ or $(Me_2CHCH(Me))_2BH$ in a solvent such as THF, dichloromethane or toluene; or reducing the acid chloride with a transition metal catalyst such as Pd/C or $Pd/BaSO_4$, under hydrogen with a modifier such as 2,4-dimethylpyridine and in solvent such as THF or toluene. Preferred conditions include reducing the ester with DIBAL in dichloromethane or toluene.

A compound of the formula (1) may be prepared by reductive amination using the aldehyde of the formula (XVI) and the amine of the formula (VIA), or salt thereof. Typically the reaction may be performed by reacting the aldehyde with 0.8–1.5 mol eq. of the amine, or salt thereof, optionally in the presence of 0.1–3 mol eq. of a protic acid, with either a reducing agent such as sodium triacetoxyborohydride or sodium cyanoborohydride, or using a catalytic transition metal catalyst such as palladium, platinum or rhodium and a hydrogen source such as molecular hydrogen or ammonium formate, in a suitable solvent such as dichloromethane, acetonitrile, toluene, ethanol or 2-propanol. Preferably the aldehyde is reacted with the tosylate salt of the amine in the presence of sodium triacetoxyborohydride and a trace of acetic acid in dichloromethane at ambient temperature.

An aldehyde of the formula (XVI) may also be prepared from an alcohol of the formula:

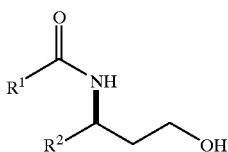

(XVIA)

by standard oxidation techniques, for example, using an oxidising agent such as DMSO/sulphur trioxide-pyridine complex, DMSO with $(COCl)_2$, $MnO_2$ or $CrO_3$, with or without a base, in a suitable solvent such as dichloromethane, toluene, acetone or acetonitrile; using a transition metal catalyst such as Rh or Ru, with or without a base, and a hydride acceptor such as a ketone, in a suitable solvent such dichloromethane, acetone, toluene or acetonitrile; or using a catalytic oxidant such as TPAP (tetrapropylammonium perruthenate) or TEMPO (2,2,6,6-tetramethyl-1-piperidinyloxy, free radical), with or without a solid support, with a stoichiometric re-oxidant for the catalyst such as NMO (4-methylmorpholine N-oxide), oxygen or sodium hypochlochlorite or hypobromite, and in a suitable solvent such as dichloromethane, acetone, toluene or acetonitrile. Preferred conditions include using DMSO, sulphur trioxide-pyridine complex and triethylamine in dichloromethane, or TEMPO, KBr, NaOCl, water and dichloromethane.

5. The compounds of the formula (I) may be prepared by reductive amination of a compound of the formula (XV) wherein Y is —CN and an amine of the formula (VIA), or salt thereof. The reduction may be performed using a transition metal catalyst, optionally in the presence of an acid, and a hydrogen source, in a suitable solvent. In a typical procedure palladium-on-charcoal or platinum (IV) oxide and a solvent such as methanol, acetic acid or 2-propanol are used.

6. The compounds of the formula (I) may be prepared by alkylation of an amine of the formula (VIA), or a salt (acid addition or metal salt) thereof, using a compound of the formula:

(XVII)

wherein $Z^1$ is a leaving group such as halo, $C_1$–$C_4$ alkanesulphonyloxy, benzenesulphonyloxy or p-toluenesulphonyloxy, optionally in the presence of a base and/or a phase transfer catalyst.

The reaction may typically be carried out in the presence of a base such as triethylamine or N,N-diisopropylethylamine; DBU (1,8-diazabicyclo[5,4,0]undec-7-ene; or an inorganic base such as $Na_2CO_3$, $NaHCO_3$, $K_2CO_3$ or $Cs_2CO_3$: optionally in the presence of a phase transfer catalyst, and in a solvent such as acetonitrile, DMF (dimethylformamide), DMSO (dimethylsulphoxide), 1,4-dioxane, THF or toluene. Alternatively, a metal salt of the amine (i.e. a deprotonated form) may be reacted with a compound of the formula (XVII) in a suitable solvent such as THF, DMF or 1,4-dioxane. Preferably the reaction is carried out by reacting the amine and a compound of the formula (XVII) with either DBU in acetonitrile or $K_2CO_3$ and 18-crown-6(1,4,7,10,13,16-hexaoxacyclooctadecane) in THF.

7. The compounds of the formula (I) may be prepared as shown in Scheme 5.

Scheme 5

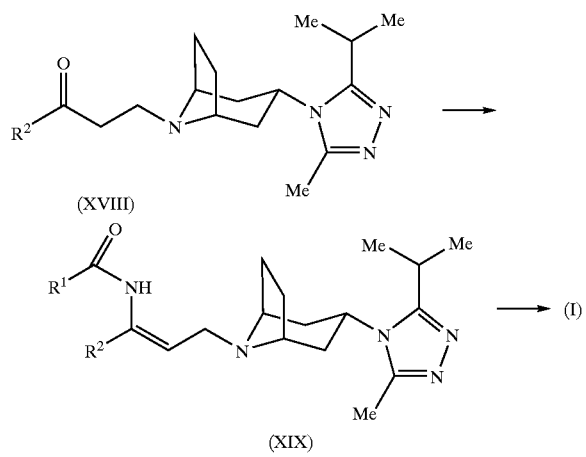

A compound of the formula (XVIII) may be prepared by the Mannich reaction of a compound of the formula:

$R^2COCH_3$ (XX)

with a compound of the formula (VIA), or salt thereof, formaldehyde or an equivalent thereof, with or without acid present, in a suitable solvent. Typical conditions include reacting the amine and the ketone with an acid such as hydrochloric acid, sulphuric acid, p-toluenesulphonic-acid or acetic acid, and paraformaldehyde in a suitable solvent such as ethanol, methanol, 2-propanol or DMF: or reacting the amine salt (such as the hydrochloride, sulphate or tosylate salt) with the ketone and paraformaldehyde in a in a suitable solvent such as ethanol, methanol, 2-propanol or DMF.

Alternatively a compound of the formula (XVIII) may be prepared by reacting a compound of the formula (VIA), or salt thereof, with a compound of the formula:

$R^2COCH_2CH_2Z^2$ (XXI)

wherein $Z^2$ is a leaving group such as as previously defined for $Z^1$, using standard alkylation conditions such as as described for Method 6 above.

An enamide of the formula (XIX) may be prepared by reaction of a compound of the formula (XVIII) with an amide of the formula:

$R^1CONH_2$ (XXII)

under dehydration conditions, with or without an acid catalyst present, and in a suitable solvent; or by reaction of a compound of the formula (XVIII) first with hydroxylamine, or salt thereof, and then reacting the intermediate product with an acid anhydride of the formula:

$(R_1CO)_2O$ (XXIII)

a transition metal catalyst, and an acid in a suitable solvent; or by reacting a compound of the formula (XVIII) first with ammonia, or a salt thereof, and then reacting the intermediate product with an acid of the formula (III), or an activated derivative thereof, under standard conditions.

Typically a compound of the formula (XVIII) is reacted with an amide of the formula (XXII) in the presence of a catalytic amount of acid with azeotropic removal of water or removal of water using a dehydrating agent such as molecular sieves.

A compound of the formula (I) may be prepared by asymmetric reduction of an enamide of the formula (XIX) such as by using 0.001–0.1 mol eq. of transition metal such as Rh, Ru, Pd, Pt, Ir, or Ti, 0.001–0.2 mol eq. of a chiral ligand such as BINAP (2,2-bis(diphenylphosphino)-1,1'-binaphthyl), tol-BINAP (2,2-bis(di-p-tolylphosphino)-1,1'-binaphthyl), Du-PHOS (1,2-bis(2,5-dimethylphospholano) benzene) or Penn-Phos (P,P'-1,2-phenylenebis(endo-2,5-dimethyl-7-phosphabicyclo[2,2,1]heptane), a hydrogen donor such as molecular hydrogen, phenylsilane, 2-propanol or ammonium formate, and a suitable solvent such as methanol, ethanol, acetonitrile, toluene, ethyl acetate, 2-propanol or THF, at from 0° C. to the reflux temperature and optionally at an elevated pressure.

8. A compound of the formula (I) may be prepared as shown in Scheme 6.

wherein $R^5$ is an ester-forming group such as $C_1$–$C_6$ alkyl. Typically the reaction may be carried out by reacting the ester and the amine, or metal salt thereof, with an excess of a base such as triethylamine and an optional catalyst in a solvent such as dichloromethane, ethyl acetate, THF or toluene, with or without water present as a co-solvent: or by reacting the ester and the amine in the presence of an enzyme-catalyst in a solvent such as dichloromethane, ethyl acetate, THF or toluene, with or without water present as a co-solvent.

All of the above reactions and the preparations of novel starting materials using in the preceding methods are conventional and appropriate reagents and reaction conditions for their performance or preparation as well as procedures for isolating the desired products will be well-known to those skilled in the art with reference to literature precedents and the Examples and Preparations hereto.

A pharmaceutically acceptable salt of a compound of the formula (I) may be readily prepared by mixing together solutions of a compound of the formula (I) and the desired Scheme 6

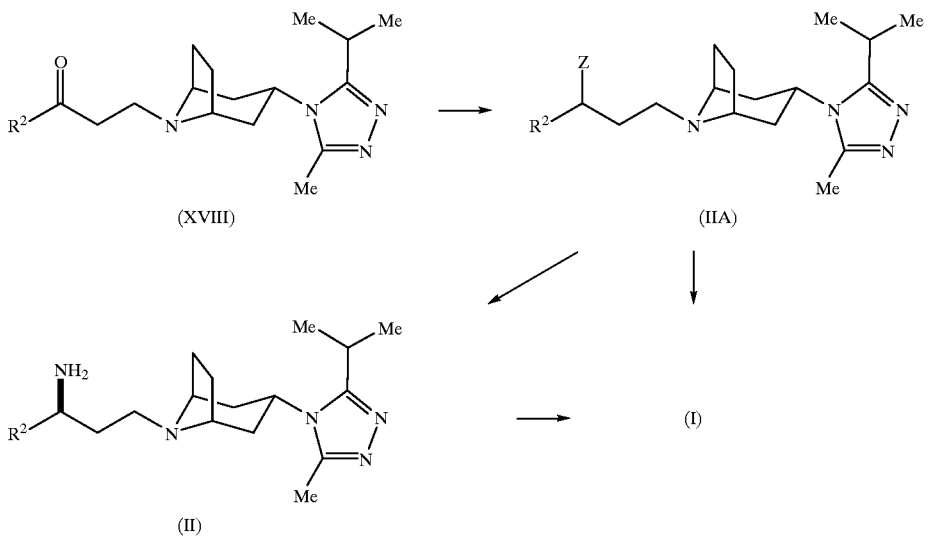

A ketone of the formula (XVIII) may be converted to a racemic amine of the formula (IIA) by reductive amination under conventional conditions using ammonia, or equivalent thereof, and a reducing agent in a suitable solvent.

The racemic amine of the formula (IIA) may be resolved to provide an amine of the formula (II) by standard techniques such as by using classical, kinetic or dynamic resolution techniques.

The amine of the formula (II) may be converted to a compound of the formula (I) by the routes described in Methods 1 and 2.

Alternatively, a racemic amine of the formula (IIA) may be converted to a compound of the formula (I) using a compound of the formula (III), or a suitable activated derivative thereof, a chiral catalyst, optionally using a catalyst for racemization of the unwanted isomer present, and a suitable solvent.

The amine of the formula (II), or a metal salt thereof (i.e. a deprotonated form), may also be converted to a compound of the formula (I) by reaction with an ester of the formula:

$$R^1CO_2R^5 \qquad (XXIV)$$

acid. The salt may precipitate from solution and be collected by filtration or may be recovered by evaporation of the solvent.

The compounds of formula (I), and their pharmaceutically acceptable salts, are useful because they have pharmacological activity in animals, including humans. More particularly, they are useful in the treatment of a disorder in which the modulation of CCR5 receptors is implicated. Disease states that may be mentioned include HIV, a retroviral infection genetically related to HIV, AIDS, or an inflammatory disease. The compounds of formula (I), and their pharmaceutically acceptable salts, may be administered alone or as part of a combination therapy.

The compounds of this invention may be used for treatment of respiratory disorders, including adult respiratory distress syndrome (ARDS), bronchitis, chronic bronchitis, chronic obstructive pulmonary disease, cystic fibrosis, asthma, emphysema, rhinitis and chronic sinusitis. Other conditions that may be treated are those triggered, affected or are in any other way correlated with T-cell trafficking in different organs. It is expected that the compounds of this invention may be useful for the treatment of such conditions and in particular, but not limited to the following for which a correlation with CCR5 or CCR5 chemokines has been established: inflammatory bowel disease, including Crohn's disease and ulcerative colitis, multiple sclerosis, rheumatoid arthritis, graft rejection, in particular but not limited to kidney and lung allografts, endometriosis, type I diabetes, renal diseases, chronic pancreatitis, inflammatory lung conditions or chronic heart failure. For a recent review of possible applications of chemokines and chemokine receptor blockers see Cascieri, M. A., and Springer, M. S., "The chemokine/chemokine receptor family: potential and progress for therapeutic intervention", Curr. Opin. Chem. Biol., 4(4), 420–7 (Aug. 2000).

The utility of the compounds of formula (I), and their pharmaceutically acceptable salts, as inhibitors of HIV infection may be demonstrated by any one or more methodologies known in the art, such as by using the HIV microculture assays described in Dimitrov et al., J. Clin. Microbiol., 28, 734–737 (1990), and the pseudotyped HIV reporter assay described in Connor et al., Virology, 206 (2) 935–44 (1995).

The ability of the compounds of formula (I), and their pharmaceutically acceptable salts, to modulate chemokine receptor activity is demonstrated by methodology known in the art, such as by using the assay for CCR5 binding following procedures disclosed in Combadiere et al., J. Leukoc. Biol., 60, 147–52 (1996); and/or by using the intracellular calcium mobilisation assays as described by the same authors. Cell lines expressing the receptor of interest include those naturally expressing the receptor, such as PM-1, or IL-2 stimulated peripheral blood lymphocytes (PBL), or a cell engineered to express a recombinant receptor, such as CHO, 300.19, L1.2 or HEK-293.

The compounds of the formula (I) can be administered alone but will generally be administered in admixture with a suitable pharmaceutical excipient, diluent or carrier selected with regard to the intended route of administration and standard pharmaceutical practice.

For example, the compounds of the formula (I) can be administered orally, buccally or sublingually in the form of tablets, capsules, multi-particulates, gels, films, ovules, elixirs, solutions or suspensions, which may contain flavouring or colouring agents, for immediate-, delayed-, modified-, sustained-, pulsed- or controlled-release applications. The compounds of the formula (I) may also be administered as fast-dispersing or fast-dissolving dosage forms or in the form of a high energy dispersion or as coated particles. Suitable formulations of the compounds of the formula (I) may be in coated or uncoated form, as desired.

Such solid pharmaceutical compositions, for example, tablets, may contain excipients such as microcrystalline cellulose, lactose, sodium citrate, calcium carbonate, dibasic calcium phosphate, glycine and starch (preferably corn, potato or tapioca starch), disintegrants such as sodium starch glycollate, croscarmellose sodium and certain complex silicates, and granulation binders such as polyvinylpyrrolidone, hydroxypropylmethylcellulose (HPMC), hydroxypropylcellulose (HPC), sucrose, gelatin and acacia. Additionally, lubricating agents such as magnesium stearate, stearic acid, glyceryl behenate and talc may be included.

General Example

A formulation of the tablet could typically contain from 0.01 mg to 500 mg of active compound whilst tablet fill weights may range from 50 mg to 1000 mg. An example of a formulation for a 10 mg tablet is illustrated below:

| Ingredient | % w/w |
| --- | --- |
| Compound of the formula (I) or salt | 10.000* |
| Lactose | 64.125 |
| Starch | 21.375 |
| Croscarmellose sodium | 3.000 |
| Magnesium stearate | 1.500 |

*Quantity adjusted in accordance with drug activity.

The tablets are manufactured by a standard process, for example, direct compression or a wet or dry granulation process. The tablet cores may be coated with appropriate overcoats.

Solid compositions of a similar type may also be employed as fillers in gelatin or HPMC capsules. Preferred excipients in this regard include lactose, starch, a cellulose, milk sugar or high molecular weight polyethylene glycols. For aqueous suspensions and/or elixirs, the compounds of the formula (I) may be combined With various sweetening or flavouring agents, colouring matter or dyes, with emulsifying and/or suspending agents and with diluents such as water, ethanol, propylene glycol and glycerin, and combinations thereof.

The compounds of the formula (I) can also be administered parenterally, for example, intravenously, intraarterially, intraperitoneally, intrathecally, intraventricularly, intraurethrally, intrasternally, intracranially, intramuscularly or subcutaneously, or they may be administered by infusion or needleless injection techniques. For such parenteral administration they are best used in the form of a sterile aqueous solution which may contain other substances, for example, enough salts or glucose to make the solution isotonic with blood. The aqueous solutions should be suitably buffered (preferably to a pH of from 3 to 9), if necessary. The preparation of suitable parenteral formulations under sterile conditions is readily accomplished by standard pharmaceutical techniques well-known to those skilled in the art. For oral or parenteral administration to human patients the daily dosage levels of compounds of formula (I), and their pharmaceutically acceptable salts, will be from 0.01 to 30 mg/kg (in single or divided doses) and preferably will be in the range 0.01 to 15 mg/kg. Thus tablets will contain 1 mg to 0.5 g of compound for administration singly or two or more at a time, as appropriate. The physician in any event will determine the actual dosage which will be most suitable for any individual patient and it will vary with the age, weight and response of the particular patient. The above dosages are exemplary of the average case. There can, of course, be individual instances where higher or lower dosage ranges are merited and such are within the scope of this invention.

Oral administration is preferred. Preferably, administration takes place shortly before an effect is required.

The compounds of formula (I) can also be administered intranasally or by inhalation and are conveniently delivered in the form of a dry powder inhaler or an aerosol spray presentation from a pressurised container, pump, spray, atomiser or nebuliser, with or without the use of a suitable propellant, e.g. dichlorodifluoromethane, trichlorofluoromethane, dichlorotetrafluoroethane, a hydrofluoroalkane such as 1,1,1,2-tetrafluoroethane (HFA 134A [trade mark]) or 1,1,1,2,3,3,3-heptafluoropropane (HFA 227EA [trade mark]), carbon dioxide or other suitable gas. In the case of a pressurised aerosol, the dosage unit may be determined by providing a valve to deliver a metered amount. The pressurised container, pump, spray, atomiser or nebuliser may contain a solution or suspension of the active compound, e.g. using a mixture of ethanol and the propellant as the solvent, which may additionally contain a lubricant, e.g. sorbitan trioleate. Capsules and cartridges (made, for example, from gelatin) for use in an inhaler or insufflator may be formulated to contain a powder mix of a compound of the formula (I) and a suitable powder base such as lactose or starch.

Aerosol or dry powder formulations are preferably arranged so that each metered dose or "puff" contains from 1 μg to 10 mg of a compound of the formula (I) for delivery to the patient. The overall daily dose with an aerosol will be in the range of from 1 μg to 20 mg which may be administered in a single dose or, more usually, in divided doses throughout the day.

Alternatively, the compounds of the formula (I) can be administered in the form of a suppository or pessary, or they may be applied topically in the form of a gel, hydrogel, lotion, solution, cream, ointment or dusting powder. The compounds of the formula (I) may also be dermally or transdermally administered, for example, by the use of a skin patch. They may also be administered by the pulmonary or rectal routes.

They may also be administered by the ocular route, particularly for treating inflammatory conditions or diseases of the eye. For ophthalmic use, the compounds can be formulated as micronised suspensions in isotonic, pH adjusted, sterile saline, or, preferably, as solutions in isotonic, pH adjusted, sterile saline, optionally in combination with a preservative such as a benzylalkonium chloride. Alternatively, they may be formulated in an ointment such as petrolatum.

For application topically to the skin, the compounds of the formula (I) can be formulated as a suitable ointment containing the active compound suspended or dissolved in, for example, a mixture with one or more of the following: mineral oil, liquid petrolatum, white petrolatum, propylene glycol, polyoxyethylene polyoxypropylene compound, emulsifying wax and water. Alternatively, they can be formulated as a suitable lotion or cream, suspended or dissolved in, for example, a mixture of one or more of the following: mineral oil, sorbitan monostearate, a polyethylene glycol, liquid paraffin, polysorbate 60, cetyl esters wax, cetearyl alcohol, 2-octyldodecanol, benzyl alcohol and water.

The compounds of the formula (I) may also be used in combination with a cyclodextrin. Cyclodextrins are known to form inclusion and non-inclusion complexes with drug molecules. Formation of a drug-cyclodextrin complex may modify the solubility, dissolution rate, bioavailability and/or stability property of a drug molecule. Drug-cyclodextrin complexes are generally useful for most dosage forms and administration routes. As an alternative to direct complexation with the drug the cyclodextrin may be used as an auxiliary additive, e.g. as a carrier, diluent or solubiliser. Alpha-, beta- and gamma-cyclodextrins are most commonly used and suitable examples are described in WO-A-91/11172, WO-A-94/02518 and WO-A-98/55148.

The compounds of formula (I), and their pharmaceutically acceptable salts, have the advantage that they are more selective, have a more rapid onset of action, are more potent, are more stable, are more resistant to metabolism, or have other more desirable properties than the compounds of the prior art.

Included within the scope of the present invention are embodiments comprising coadministration of, and compositions which contain, in addition to a compound of the present invention as active ingredient, additional therapeutic agents and active ingredients. Such multiple drug regimens, often referred to as combination therapy, may be used in the treatment and prevention of any of the diseases or conditions mediated by or associated with CCR5 chemokine receptor modulation, particularly infection by human immunodeficiency virus, HIV. The use of such combinations of therapeutic agents is especially pertinent with respect to the treatment and prevention of infection and multiplication of the human immunodeficiency virus, HIV, and related pathogenic retroviruses within a patient in need of treatment or one at risk of becoming such a patient. The ability of such retroviral pathogens to evolve within a relatively short period of time into strains resistant to any monotherapy which has been administered to said patient is well known in the literature.

In addition to the requirement of therapeutic efficacy which may necessitate the use of active agents in addition to the CCR5 chemokine receptor modulating compounds of formula (I), and their pharmaceutically acceptable salts, there may be additional rationales which compel or highly recommend the use of combinations of drugs involving active ingredients which represent adjunct therapy, i.e., which complement and supplement the function performed by the CCR5 chemokine receptor modulating compounds of the present invention. Such supplementary therapeutic agents used for the purpose of auxiliary treatment include drugs which, instead of directly treating or preventing a disease or condition mediated by or associated with CCR5 chemokine receptor modulation, treat diseases or conditions which directly result from or indirectly accompany the basic or underlying CCR5 chemokine receptor modulated disease or condition. For example, where the basic CCR5 chemokine receptor modulated disease or condition is HIV infection and multiplication, it may be necessary or at least desirable to treat opportunistic infections, neoplasms, and other conditions which occur as the result of the immune-compromised state of the patient being treated. Other active agents may be used with the compounds of formula (I), and their pharmaceutically acceptable salts, e.g., in order to provide immune stimulation or to treat pain and inflammation which accompany the initial and fundamental HIV infection.

Thus, the methods of treatment and pharmaceutical compositions of the present invention may employ the compounds of formula (I), and their pharmaceutically acceptable salts, in the form of monotherapy, but said methods and compositions may also be used in the form of multiple therapy in which one or more compounds of formula (I), or their pharmaceutically acceptable salts, are coadministered in combination with one or more known therapeutic agents such as those described in detail further herein.

Preferred combinations of the present invention include simultaneous, or sequential treatments with a compound of formula (I), or a pharmaceutically acceptable salt thereof, and one or more inhibitors of HIV protease and/or inhibitors of HIV reverse transcriptase, preferably selected from the class of non-nucleoside reverse transcriptase inhibitors (NNRTI), including but not limited to nevirapine, delavirdine and efavirenz; from among the nucleoside/nucleotide inhibitors, including but not limited to zidovudine, didanosine, zalcitabine, stavudine, lamivudine, abacavir, adefovir and dipivoxil; and from among the protease inhibitors, including but not limited to indinavir, ritonavir, saquinavir, nelfinavir, lopinavir and amprenavir. Other agents useful in the above-described preferred embodiment combinations of the present invention include current and to-be-discovered investigational drugs from any of the above classes of inhibitors, including but not limited to FTC, PMPA, fozivudine tidoxil, talviraline, S-1153, MKC442, MSC-204, MSH-372, DMP450, PNU-140690, ABT-378 and KNI-764. There is also included within the scope of the preferred embodiments of the present invention, combinations of a compound of formula (I), or a pharmaceutically acceptable salt thereof, together with a supplementary therapeutic agent used for the purpose of auxiliary treatment, wherein said supplementary therapeutic agent comprises one or more members independently selected from the group consisting of proliferation inhibitors, e.g., hydroxyurea; immunomodulators, e.g., sargramostim, and various forms of interferon or interferon derivatives; fusion inhibitors, e.g., AMD3100, T-20, PRO-542, AD-349, BB-10010 and other chemokine receptor agonists/antagonists; tachykinin receptor modulators, e.g. NK1 antagonists; integrase inhibitors, e.g., AR177; RNaseH inhibitors; inhibitors of viral transcription and RNA replication; and other agents that inhibit viral infection or improve the condition or outcome of HIV-infected individuals through different mechanisms.

Preferred methods of treatment of the present invention for the prevention of HIV infection, or treatment of aviremic and asymptomatic subjects potentially or effectively infected with HIV, include but are not limited to administration of a member independently selected from the group consisting of: (i) a compound within the scope of formula (I) as disclosed herein; (ii) one NNRTI in addition to a compound of (i); (iii) two NRTI in addition to a compound of (i); (iv) one NRTI in addition to the combination of (ii); and (v) a compound selected from the class of protease inhibitors used in place of a NRTI in combinations (iii) and (iv).

The preferred methods of the present invention for therapy of HIV-infected individuals with detectable viremia or abnormally low CD4 counts further include as a member to be selected: (vi) treatment according to (i) above in addition to the standard recommended initial regimens for the therapy of established HIV infections, e.g., see http://hivatis.org/trtgdlns.html. Such standard regimens include but are not limited to an agent from the class of protease inhibitors in combination with two NRTIs; and (vii) a standard recommended initial regimens for the therapy of established HIV infections, e.g., see http://hivatis.org/trtgdlns.html, where either the protease inhibitor component, or one or both of the NRTIs is/are replaced by a compound within the scope of formula (I) as disclosed herein.

The preferred methods of the present invention for therapy of HIV-infected individuals that have failed antiviral therapy further include as a member to be selected: (viii) treatment according to (i) above, in addition to the standard recommended regimens for the therapy of such patients, e.g., see http://hivatis.org/trtgdlns.html; and (ix) a standard recommended initial regimens for the therapy of patients who have failed antiretroviral therapy, e.g., see http://hivatis.org/trtgdlns.html, where either one of the protease inhibitor components, or one of both of the NRTIs is/are replaced by a compound within the scope of formula (I) as disclosed herein.

In the above-described preferred embodiment combinations of the present invention, the compound of formula (I) and other therapeutic active agents may be administered in terms of dosage forms either separately or in conjunction with each other, and in terms of their time of administration, either serially or simultaneously. Thus, the administration of one component agent may be prior to, concurrent with, or subsequent to the administration of the other component agent(s).

It is to be appreciated that all references herein to treatment include curative, palliative and prophylactic treatment.

Thus the invention provides:

a compound of the formula (I) or a pharmaceutically acceptable salt or solvate thereof;

processes for the preparation of a compound of the formula (I) or a pharmaceutically acceptable salt or solvate thereof;

a pharmaceutical composition including a compound of the formula (I) or a pharmaceutically acceptable salt or solvate thereof, together with a pharmaceutically acceptable excipient, diluent or carrier;

a compound of the formula (I) or a pharmaceutically acceptable salt, solvate or composition thereof, for use as a medicament;

a compound of the formula (I) or a pharmaceutically acceptable salt, solvate or composition thereof, for the treatment of a disorder in which the modulation of CCR5 receptors is implicated;

a compound of the formula (I) or a pharmaceutically acceptable salt, solvate or composition thereof, for the treatment of HIV, a retroviral infection genetically related to HIV, AIDS, or an inflammatory disease;

a compound of the formula (I) or a pharmaceutically acceptable salt, solvate or composition thereof, for the treatment of a respiratory disorder including adult respiratory distress syndrome (ARDS), bronchitis, chronic bronchitis, chronic obstructive pulmonary disease, cystic fibrosis, asthma, emphysema, rhinitis or chronic sinusitis;

a compound of the formula (I) or a pharmaceutically acceptable salt, solvate or composition thereof, for the treatment of an inflammatory bowel disease, including Crohn's disease or ulcerative colitis, multiple sclerosis, rheumatoid arthritis, graft rejection, including a kidney or a lung allograft, endometriosis, type I diabetes, a renal disease, chronic pancreatitis, an inflammatory lung condition or chronic heart failure;

the use of a compound of the formula (I) or of a pharmaceutically acceptable salt, solvate or composition thereof, for the manufacture of a medicament for the treatment of a disorder in which the modulation of CCR5 receptors is implicated;

the use of a compound of the formula (I) or of a pharmaceutically acceptable salt, solvate or composition thereof, for the manufacture of a medicament for the treatment of HIV, a retroviral infection genetically related to HIV, AIDS, or an inflammatory disease;

the use of a compound of the formula (I) or of a pharmaceutically acceptable salt, solvate or composition thereof, for the manufacture of a medicament for the treatment of a respiratory disorder including adult respiratory distress syndrome (ARDS), bronchitis, chronic bronchitis, chronic obstructive pulmonary disease, cystic fibrosis, asthma, emphysema, rhinitis or chronic sinusitis; the use of a compound of the formula (I) or of a pharmaceutically acceptable salt, solvate or composition thereof, for the manufacture of a medicament for the treatment of an inflammatory bowel disease, including Crohn's disease or ulcerative colitis, multiple sclerosis, rheumatoid arthritis, graft rejection, including a kidney or a lung allograft, endometriosis, type I diabetes, a renal disease, chronic pancreatitis, an inflammatory lung condition or chronic heart failure;

a method of treatment of a mammal to treat a disorder in which the modulation of CCR5 receptors is implicated including treating said mammal with an effective amount of a compound of the formula (I) or with a pharmaceutically acceptable salt, solvate or composition thereof;

a method of treatment of a mammal to treat HIV, a retroviral infection genetically related to HIV, AIDS, or an inflammatory disease including treating said mammal with an effective amount of a compound of the formula (I) or with a pharmaceutically acceptable salt, solvate or composition thereof;

a method of treatment of a mammal to treat a respiratory disorder including adult respiratory distress syndrome (ARDS), bronchitis, chronic bronchitis, chronic obstructive pulmonary disease, cystic fibrosis, asthma, emphysema, rhinitis or chronic sinusitis including treating said mammal with an effective amount of a compound of the formula (I) or with a pharmaceutically acceptable salt, solvate or composition thereof;

a method of treatment of a mammal to treat an inflammatory bowel disease, including Crohn's disease or ulcerative colitis, multiple sclerosis, rheumatoid arthritis, graft rejection, including a kidney or a lung allograft, endometriosis, type I diabetes, a renal disease, chronic pancreatitis, an inflammatory lung condition or chronic heart failure including treating said mammal with an effective amount of a compound of the formula (I) or with a pharmaceutically acceptable salt, solvate or composition thereof; and intermediates of the formulae (II), (IIA), (VII), (VIA), (XII), (XIV), (XVIII) and (XIX).

The invention is illustrated by the following Examples, in which the following abbreviations may be used:
0.88 ammonia=concentrated ammonium hydroxide solution, 0.88 SG
h=hour
min=minute
MS=mass spectrum
NMR=nuclear magnetic resonance
Me=methyl

EXAMPLE 1

N-{(1S)-3-[3-(3-Isopropyl-5-methyl-4H-1,2,4-triazol-4-yl)-exo-8-azabicyclo[3.2.1]oct-8-yl]-1-phenylpropyl}cyclobutanecarboxamide N-Benzyl-N'-cyclohexylcarbodiimide-polymer bound (1.15 g, 0.88 mmol) was added to a solution of the title compound from Preparation 11 (250 mg, 0.68 mmol) and cyclobutanecarboxylic acid (130 µl, 1.37 mmol) in dichloromethane (10 ml) and the mixture stirred at room temperature for 16 hours. The mixture was filtered through Celite® (filtration aid) and evaporated under reduced pressure. The residue was purified by column chromatography on silica gel, using an elution gradient of dichloromethane:methanol: 0.88 ammonia (1:0:0 to 95:5:0.5, by volume) to afford the title compound as a white foam, 200 mg.

Found C, 69.98; H, 8.67; N, 14.89%

$C_{27}H_{39}N_5O$; 0.2 $CH_2Cl_2$; requires C, 70.01; H, 8.51; N, 15.01%

$^1$H-NMR (400 MHz, CDCl$_3$): δ [ppm] 1.40 (6H, d), 1.63 (4H, m), 1.85–2.45 (14H, m), 2.52 (3H, s), 3.00 (2H, m), 3.39 (2H, m), 4.30 (1H, m), 5.15 (1H, m 6.35 (1H, m), 7.15–7.40 (5H, m).

LRMS: m/z 450.3 (MH$^+$)

$[α]_D$ –34.0° (c=0.10, MeOH)

EXAMPLE 2

N-{(1S)-3-[3-(3-Isopropyl-5-methyl-4H-1,2,4-triazol-4-yl)-exo-8-azabicyclo[3.2.1]oct-8-yl]-1-phenylproyl}cyclopentanecarboxamide Cyclopentanecarboxylic acid (115 µl, 1.06 mmol) was added to a solution of the title compound from Preparation 11 (300 mg, 0.82 mmol), hydroxybenzotriazole hydrate (10 mg, 74 µmol) and 1-(3-dimethylaminopropyl)-3-ethylcarbodiimide methiodide (300 mg, 1.07 mmol) in dichloromethane (10 ml) and the mixture stirred at room temperature for 3 hours. Saturated aqueous sodium carbonate solution (50 ml) was added to the mixture and the product was extracted with dichloromethane (2×). The combined organic layers were washed with brine, dried (MgSO$_4$), filtered and evaporated under reduced pressure. The residue was purified by column chromatography on silica gel using an elution gradient of dichloromethane:methanol: 0.88 ammonia (1:0:0 to 96:4:0.4, by volume) to afford the title compound as a white foam, 330 mg.

Found C, 69.73; H, 9.00; N, 14.09% $C_{28}H_{41}N_5O$; 0.25 $CH_2Cl_2$; requires C, 69.98; H, 8.63; N, 14.44%.

$^1$H-NMR (400 MHz, CDCl$_3$): δ [ppm]1.35 (6H, d), 1.51–2.04 (16H, m), 2.17 (2H, m), 2.39 (2H, m), 2.45 (4H, m), 2.95 (1H, m), 3.36 (2H, s), 4.25 (1H, m), 5.09 (1H, m), 6.12 (1H, m), 7.20–7.33 (5H, m).

LRMS: m/z 464.8 (MH$^+$)

$[α]_D$ –29.21° (c=0.10, MeOH)

Melting point [° C.]: 68–70

EXAMPLE 3

N-{(1S)-3-[3-(3-Isopropyl-5-methyl-4H-1,2,4-triazol-4-yl)-exo-8-azabicyclo[3.2.1]oct-8-yl]-1-phenylproyl}-4,4,4-trifluorobutanamide

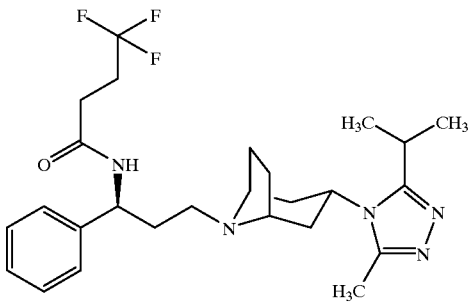

N-Benzyl-N'-cyclohexylcarbodiimide-polymer bound (370 mg, 0.336 mmol) was added to a solution of the title compound from Preparation 11 (100 mg, 0.27 mmol) and 4,4,4-trifluorobutanecarboxylic acid (45 mg, 0.32 mmol) in dichloromethane (4 ml) and the mixture was stirred at room temperature for 1.5 hours. The mixture was filtered through Celite® and evaporated under reduced pressure. The residue was purified by column chromatography on silica gel using an elution gradient of dichloromethane: methanol: 0.88 ammonia (1:0:0 to 95:5:0.5, by volume) to afford the title compound as a white foam, 75 mg.

Found C, 61.55; H, 7.46; N, 13.62% $C_{26}H_{36}N_5OF_3$;0.25 $CH_2Cl_2$; requires C, 61.48; H, 7.17; N, 13.66%

$^1$H-NMR (400 MHz, CDCl$_3$): δ [ppm] 1.39 (6H, d), 1.65 (5H, m), 1.98 (2H, m 2.07 (2H, m), 2.15–2.29 (2H, m), 2.43 (5H, m), 2.52 (3H, s), 3.00 (1H, m), 3.40 (2H, s), 4.30 (1H, m), 5.15 (1H, m), 6.94 (1H, m), 7.28 (3H, m), 7.36 (2H, m)

LRMS: m/z 492.3 (MH$^+$)

[α]$^D$ −32.41° (c=0.10, MeOH)

EXAMPLE 4

N-{(1S)-3-[3-(3-Isopropyl-5-methyl-4H-1,2,4-triazol-4-yl)-exo-8-azabicyclo[3.2.1]oct-8-yl]-1-phenylpropyl}-4,4-difluorocyclohexanecarboxamide

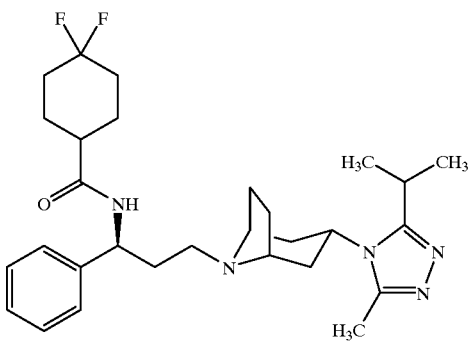

N-Benzyl-N'-cyclohexylcarbodiimide-polymer bound (500 mg, 0.545 mmol) was added to a solution of the title compound from Preparation 11 (100 mg, 0.27 mmol) and 4,4-difluorocyclohexanecarboxylic acid (50 mg, 0.30 mmol) in dichloromethane (4 ml) and the mixture was stirred at room temperature for 1.5 hours. The mixture was filtered through Celite® and evaporated under reduced pressure. The residue was purified by column chromatography on silica gel using an elution gradient of dichloromethane: methanol: 0.88 ammonia (1:0:0 to 95:5:0.5, by volume) to afford the title compound as a white foam, 67 mg.

Found C, 64.68; H, 7.88; N, 12.65% $C_{29}H_{41}N_5OF_2$;1.36 $H_2O$; requires C, 64.72; H, 8.19; N, 13.01%

$^1$H-NMR (400 MHz, CDCl$_3$): δ [ppm] 1.39 (6H, d), 1.61–2.18 (19H, m), 2.28 (2H, m), 2.48 (3H, s), 2.85 (1H, m), 3.36 (2H, br d), 4.28 (1 H, m), 5.15 (I H, m), 6.48–6.61 (1 H, br m), 7.23 (3H, m), 7.36 (2H, m)

LRMS: m/z 514.4 (MH$^+$)

PXRD analysis showed the product to be a mixture of polymorphs termed "Form A" and "Form B". Single crystals of pure Form A and Form B could be identified and separated from the mixture. The PXRD data for Forms A and B are listed in Appendix 1.

EXAMPLE 5

N-{(1S)-3-[3-(3-Isopropyl-5-methyl-4H-1,2,4-triazol-4-yl)-exo-8-azabicyclo[3.2.1]oct-8-yl]-1-(3-fluorophenyl)propyl}4,4-difluorocyclohexanecarboxamide

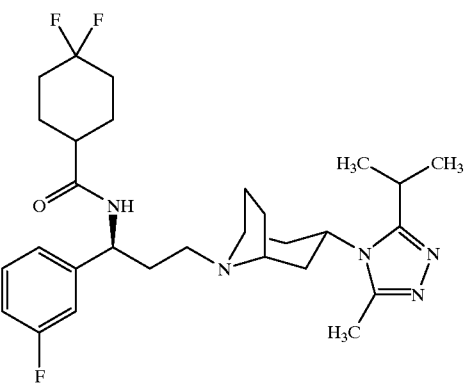

The title compound was prepared from the title compound from Preparation 13 (200 mg, 0.52 mmol) and 4,4,-difluorocyclohexanecarboxylic acid (128 mg, 0.79 mmol) using a similar method to that described in Example 4, 160 mg.

Found C, 64.25; H, 7.67; N, 12.53%

$C_{29}H_{40}N_5OF_3$;0.7 $H_2O$; requires C, 64.00; H, 7.67; N, 12.87%

$^1$H-NMR (400 MHz, CDCl$_3$): δ [ppm] 1.39 (6H, d), 1.60–2.35 (19H, m), 2.42–2.60 (2H, m), 2.55 (3H, s), 2.98 (1H, m), 3.40 (2H, br d), 4.32 (1H, m), 5.14 (1H, m), 6.79 (1H, br m), 6.97 (2H, m), 7.05 (1H, m), 7.31 (1H, m).

LRMS: m/z 532 (MH$^+$).

EXAMPLE 6

N-{(1S)-3-[3-(3-Isopropyl-5-methyl-4H-1,2,4-triazol-4-yl)-exo-8-azabicyclo[3.2.1]oct-8-yl]-1-phenylpropyl}-4,4-difluorocyclohexanecarboxamide

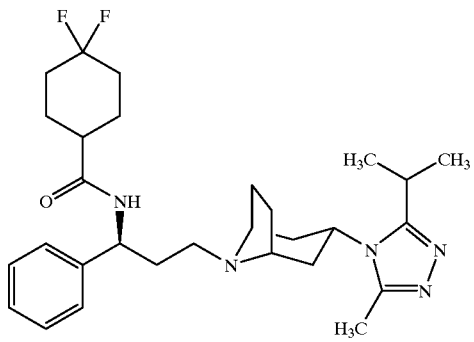

The title compound from Preparation 20 (176 g, 0.48 mol) was dissolved in dichloromethane (1.76 l). A solution of saturated aqueous sodium carbonate (1.76 l) and water (1.76 l) was added. An exotherm was observed and the mixture was cooled to 15° C. A solution of the title compound from Preparation 14 (131.6 g, 0.72 mol) in toluene (500 ml) was added to the reaction mixture and an exotherm was observed. The resultant mixture was stirred for 12 h at room temperature. HPLC analysis of the reaction mixture indicated that the reaction had reached completion. Water (1 l) and dichloromethane (1 l) were added to facilitate phase separation. The phases were separated and pH of the aqueous phase was pH=11. The aqueous phase was washed with dichloromethane (1.76 l). The combined organic phases were washed with 0.5 M aqueous sodium hydroxide (1.76 l) and then with with water (1.76 l). The organic phase was concentrated and ethyl acetate (700 ml) added. The mixture was allowed to granulate at ambient temperature over night. The white solid was filtered off and and the product was washed with ethyl acetate (60 ml) and dried in a vacuum oven for 12 h at 40° C. to give the title compound as a white solid 146 g (59%).

$^1$H-NMR was identical to the title compound in Example 4.

PXRD analysis showed the product to be a single polymorph termed "Form B". The PXRD data for Form B are listed in Appendix 1.

The melting point of Form B was determined as 197° C. (peak temperature) using a T.A. Instruments 2100 DSC. The Scan was made at 20° C./minute, (ambient to 300° C.) with nitrogen flow gas.

EXAMPLE 7

N-{(1S-3-[3-(3-Isopropyl-5-methyl-4H-1,2,4-triazol-4-yl)-exo-8-azabicyclo[3.2.1]oct-8-yl]-1-phenylpropyl}-4,4-difluorocyclohexanecarboxamide

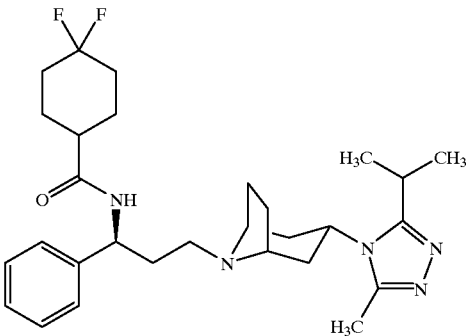

The title compound from Preparation 9 was slurried in dichloromethane (9 ml) and a solution of the title compound from Preparation 17 (1.58 g, 5.35 mmol) in toluene (3.2 ml) was added to the reaction mixture followed by addition of acetic acid (0.3 ml). To the resultant solution was added sodium triacetoxyborohydride (1.36 g, 6.24 mmol) in portions. The resultant slurry was stirred at room temperature for 30 minutes. A sample was analysed by HPLC and TLC and the reaction was deemed complete. Water (10 ml) was added followed by 2 M aqueous potassium hydroxide solution (10 ml) and the layers were separated. The aqueous phase was washed with dichloromethane (10 ml) and the combined organic layers were washed with 1 M aqueous potassium hydroxide solution (10 ml). The organic layer was concentrated under reduced pressure to yield a pale brown foam which was reslurried in ethyl acetate (10 ml) for 12 hours at room temperature. The white solid was filtered off and dried in an oven under reduced pressure at 40° C. for 4 hours to give the title compound which is identical with the title compound from Example 4, 2.05 g, 75% yield.

The following Preparations illustrate the preparation of certain intermediates used in the above Examples.

Preparation 1

Methyl (3S)-3-amino-3-phenylpropanoate

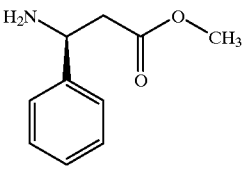

A solution of tert-butyl (3S)-3-amino-3-phenylpropanoate (5.04 g, 22.9 mmol) in 2.25 M methanolic hydrogen chloride (100 ml) was heated under reflux for 2½ hours. The mixture was cooled to room temperature, basified with saturated aqueous sodium carbonate solution to pH 8 and the phases separated. The aqueous layer was extracted with dichloromethane (4×). The combined organic solutions were washed with brine, dried (MgSO$_4$), filtered and evaporated under reduced pressure to afford the title compound, 3.97 g.

$^1$H-NMR (400MHz, CDCl$_3$): δ [ppm] 1.70 (2H, s), 2.66 (2H, d), 3.68 (3H, s), 4.43 (1H, t), 7.25–7.40 (5H, m).

LRMS: m/z 180.3 (MH$^+$).

Preparation 2

Methyl (3S)-3-[(tert-butoxycarbonyl)amino]-3-phenylpropanoate

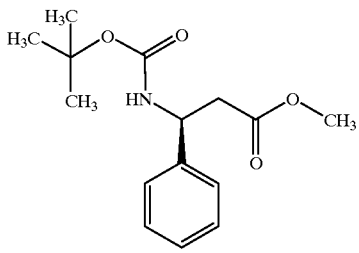

A mixture of the title compound from Preparation 1 (5.38 g, 30 mmol), di-tert-butyl dicarbonate (8.72 g, 40 mmol), tetrahydrofuran (50 ml) and 2N aqueous sodium hydroxide solution (25 ml) were stirred at room temperature for 2 hours. The reaction mixture was diluted with ethyl acetate, the layers separated and the aqueous phase extracted with ethyl acetate (2×). The combined organic solutions were washed with water, brine, dried (MgSO$_4$), filtered and evaporated under reduced pressure to afford the title compound as a white solid, 8.39 g.

$^1$H NMR (400 MHz, CDCl$_3$): δ [ppm] 1.41 (9H, s), 2.84 (2H, m), 3.61 (3H, s), 5.10 (1H, bs), 5.41 (1H, bs), 7.22–7.36 (5H, m).

LRMS: m/z 279.7 (MH$^+$)

Preparation 3 tert-Butyl (1S)-3-oxo-1-phenylpropylcarbamate

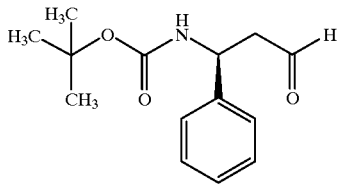

Diisobutylaluminium hydride (1 M in dichloromethane, 60 ml, 60 mmol) was cooled to −78° C. and added dropwise to a solution of the title compound from Preparation 2 (8.39 g, 30 mmol) in dichloromethane (150 ml) at −78° C. The reaction was stirred for 90 minutes then methanol (pre-cooled to −78° C., 40 ml) was added. The mixture was allowed to warm to room temperature and poured into 2 M aqueous hydrochloric acid (200 ml). The layers were separated and the aqueous phase extracted with dichloromethane (2×). The combined organic layers were dried (MgSO$_4$), filtered and evaporated under reduced pressure to afford the title compound as a white solid, 6.72 g.

$^1$H NMR (400 MHz, CDCl$_3$): δ [ppm] 1.42 (9H, s), 2.86–3.00 (2H, m), 5.06 (1H, bs), 5.20 (1H, bs), 7.22–7.38 (5H, m), 9.75 (1H, s).

LRMS: m/z 250.1 (MH$^{3O}$).

Preparation 4

8-Benzyl-8-azabicyclo[3.2.1]octan-3-one

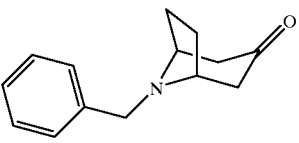

A solution of 2,5-dimethoxytetrahydrofuran (50 g, 378 mmol) in 0.025 M aqueous hydrochloric acid (160 ml) was cooled to 0° C. and stirred for 16 hours. Benzylamine hydrochloride (65 g, 453 mmol), ketomalonic acid (55 g, 377 mmol) and an aqueous solution of sodium acetate (300 ml, 0.69 M) were added and the reaction stirred at room temperature for 1 hour. The mixture was heated to 50° C. for a further 90 minutes then cooled in an ice bath and basified to pH12 with 2 N aqueous sodium hydroxide solution. The layers were separated, and the aqueous phase extracted with ethyl acetate (3×). The combined organic solutions were washed with water, dried (MgSO$_4$), filtered and evaporated under reduced pressure. The residual brown oil was distilled under reduced pressure (126° C./0.4 kPa) to afford the title compound as an off-white solid, 37.81 g.

$^1$H NMR (400 MHz, CDCl$_3$): δ [ppm] 1.64 (2H, m), 2.06–2.14 (2H, m), 2.18 (1 H, s), 2.23 (1H, s), 2.68 (1H, m), 2.72 (1H, m), 3.48 (2H, s), 3.73 (2H, s), 7.20–7.29 (1H, m), 7.32 (2H, m), 7.42 (2H, d).

LRMS: m/z 216.3 (MH$^+$).

Preparation 5

8-Benzyl-8-azabicyclo[3.2.1]octan-3-one oxime

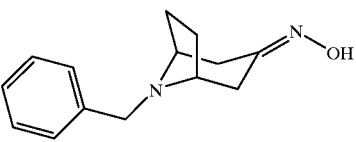

A mixture of the title compound from Preparation 4 (17.72 g, 82 mmol), hydroxylamine hydrochloride (5.72 g, 82 mmol) and pyridine (7.2 ml, 89 mmol), was heated under reflux in ethanol (500 ml) for 20 hours. The reaction was allowed to cool to room temperature and diluted with saturated aqueous sodium carbonate solution. The mixture was filtered and the filtrate evaporated under reduced pressure. The residue was partitioned between dichloromethane and water, the layers separated and the aqueous layer extracted with dichloromethane (2×). The combined organic extracts were washed with brine, dried (MgSO$_4$), filtered and evaporated under reduced pressure to afford the title compound as a pale brown solid, 18.10 g.

$^1$H NMR (400 MHz, CDCl$_3$): δ [ppm] 1.45–1.56 (1H, m), 1.60–1.67 (1H, m), 1.96–2.07 (2H, bm), 2.12 (1H, m), 2.21 (1H, m), 2.57 (1H, m), 2.97 (1H, m), 3.32 (2H, m), 3.64 (2H, s), 7.06 (1H, s), 7.21–7.28 (1H, m), 7.32 (2H, m), 7.38 (2H, d).

LRMS: m/z 231.2 (MH$^+$)

Preparation 6
8-Benzyl-8-azabicyclo[3.2.1]octan-3-exo-amine

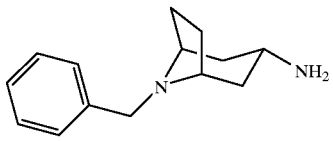

A solution of the title compound from Preparation 5 (18.10 g, 79 mmol) in pentanol (500 ml) was heated under reflux. Sodium (22.0 g, 957 mmol) was added portionwise over 2.5 hours. The reaction was then heated under reflux for a further 2 hours then cooled to 0° C. in an ice bath. Water was added until no more hydrogen gas was evolved. The mixture was acidified using 6 N aqueous hydrochloric acid and the phases separated. The organic layer was extracted with 6 N aqueous hydrochloric acid (3×), the combined aqueous extracts were basified to pH12 with sodium hydroxide pellets (400 g) and the aqueous solution extracted with ethyl acetate (3×). The combined organic solutions were dried (MgSO$_4$), filtered and evaporated under reduced pressure to afford the title compound, 15.65 g.

$^1$H NMR (400 MHz, CDCl$_3$): δ [ppm] 1.20–1.40 (2H, bm), 148 (2H, m), 1.58 (2H,d), 1.64–1.76 (2H, bm), 2.00 (2H, bm), 2.95 (1H, m), 3.19 (2H, bs), 3.57 (2H, s), 7.18–7.26 (1H, m), 7.30 (2H, m), 7.37 (2H, d).

LRMS: m/z 217.3 (MH$^+$).

Preparation 7
N-(8-Benzyl-8-azabicyclo[3.2.1]oct-3-yl-exo)-2-methylpropanamide

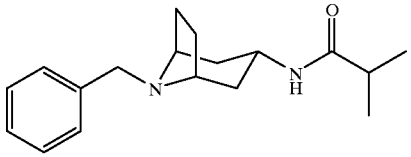

Triethylamine (9 ml, 66.8 mmol) was added to a solution of the title compound from Preparation 6 (13 g, 60.1 mmol), isobutyric acid (5.6 ml, 60.5 mmol) and 1-(3-dimethylaminopropyl)-3-ethylcarbodiimide hydrochloride (11.6 g, 60.4 mmol) in dichloromethane (150 ml). The reaction mixture was stirred at room temperature for 3 hours after which time isobutyric acid (1.4 ml, 15 mmol) and 1-(3-dimethylaminopropyl)-3-ethylcarbodiimide hydrochloride (2.9 g, 15.1 mmol) were added. The reaction mixture was stirred at room temperature for 2 days after which time isobutyric acid (2.6 ml, 28 mmol), 1-(3-dimethylaminopropyl)-3-ethylcarbodiimide hydrochloride (5 g, 26 mmol) and triethylamine (3 ml, 22.3 mmol) were added. The reaction was stirred for 24 hours. Saturated aqueous sodium carbonate solution (300 ml) was added to the mixture and the product was extracted with dichloromethane (2×). The combined organic layers were washed with brine, dried (MgSO$_4$), filtered and evaporated under reduced pressure. The residue was purified by column chromatography on silica gel using an elution gradient of dichloromethane:methanol: 0.88 ammonia (1:0:0 to 97:3:0.3, by volume) to afford the title compound as a white powder, 9.2 g.

Found C, 75.43;H, 9.30; N, 9.82% C$_{18}$H$_{26}$N$_2$O requires C, 75.48; H, 9.15; N, 9.78%

$^1$H-NMR (400 MHz, CDCl$_3$): δ [ppm] 1.10 (6H, d), 1.47 (2H, tr), 1.60 (2H, s), 1.70 (2H, m), 1.80 (2H, m), 2.02 (2H, m), 2.27 (1H, m), 3.20 (2H, s), 4.10 (1H, m), 5.15 (1H, m), 7.20–7.40 (5H, m).

LRMS: m/z 287.4 (MH$^+$)

Melting point [° C.]: 138–140

Preparation 8
8-Benzyl-3-(3-isopropyl-5-methyl-4H-1,2,4-triazol-4-yl)-exo-8-azabicyclo[3.2.1]octane

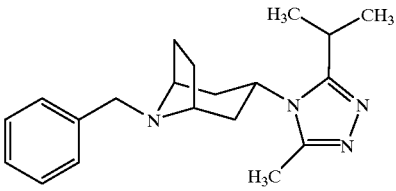

Phosphorus oxychloride (9 ml, 96.9 mmol) was added to a solution of the title compound from Preparation 7 (9.2 g, 32 mmol) and pyridine (16 ml, 196 mmol) in chloroform (20 ml) at 0° C. The reaction mixture was allowed to warm to room temperature and stirred at room temperature for 5 hours. The mixture was evaporated under reduced pressure. The residue was dissolved in chloroform (40 ml) and acetic hydrazide (3.6 g, 48.6 mmol) was added. The mixture was heated under reflux for 3 hours. Saturated aqueous sodium carbonate solution (250 ml) was added to the mixture and the product was extracted with dichloromethane (2×). The combined organic layers were washed with brine, dried (MgSO$_4$), filtered and evaporated under reduced pressure. Toluene (200 ml) and p-toluenesulphonic acid monohydrate (100 mg, 0.53 mmol) were added to the residue. The reaction mixture was heated under reflux for 2 hours. The reaction mixture was evaporated under reduced pressure. The residue was purified by column chromatography on silica gel using an elution gradient of dichloromethane: methanol: 0.88 ammonia (1:0:0 to 95:5:0.5, by volume) to afford the crude product. The crude material was suspended in 6N aqueous hydrochloric acid (40 ml) and heated under reflux for 12 hours after which time 12 N aqueous hydrochloric acid (4 ml) was added. The reaction mixture was heated under reflux for 2 hours. The mixture was evaporated under reduced pressure. The residue was basified by the addition of saturated aqueous potassium carbonate solution (200 ml) and the product was extracted with dichloromethane (3×). The combined organic layers were washed with brine, dried (MgSO$_4$), filtered and evaporated under reduced pressure. The residue was purified by column chromatography on silica gel using an elution gradient of dichloromethane:methanol: 0.88 ammonia (1:0:0 to 96:4:0.4, by volume) to afford the title compound as a white powder, 3.12 g.

$^1$H-NMR (300 MHz, CDCl$_3$): α [ppm] 1.40 (6H, d), 1.70 (4H, m), 2.15–2.40 (4H, m), 2.60 (3H, s), 3.07 (1H, m), 3.37 (2H, s), 3.60 (2H, s), 4.30 (1H, m), 7.25–7.40 (5H, m).

LRMS: m/z 325.3(MH$^+$)

Preparation 9
3-(3-Isopropyl-5-methyl-4H-1,2,4-triazol-4-yl)-exo-8-azabicyclo[3.2.1]octane

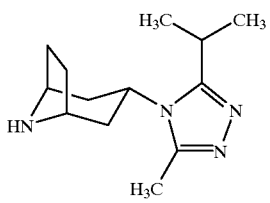

Ammonium formate (6 g, 92 mmol) was added to a solution of the title compound from Preparation 8 (3.12 g, 9.6 mmol) and palladium (II) hydroxide (500 mg) in ethanol (400 ml). The mixture was heated under reflux for 2 hours after which time 0.88 ammonia solution (2 ml) was added. The mixture was heated under reflux for 1 hour and the reaction was allowed to cool to room temperature and filtered through Arbocel™ (filtration aid). The solvent was evaporated under reduced pressure to afford the title compound as a white solid, 1.91 g $^1$H-NMR (300 MHz, CDCl$_3$): δ [ppm] 1.37 (6H, d), 1.70–2.25 (8H, m), 2.50 (3H, s), 3.05 (1H, m), 3.70 (2H, m), 4.32 (1H, m).

LRMS: m/z 235.0(MH$^+$)

Melting point [° C.]: 150–154

Preparation 10
tert-Butyl (1S)-3-[3-(3-isopropyl-5-methyl-4H-1,2,4-triazol-4-yl)-exo-8-azabicyclo[3.2.1]oct-8-yl]-1-phenylpropylcarbamate

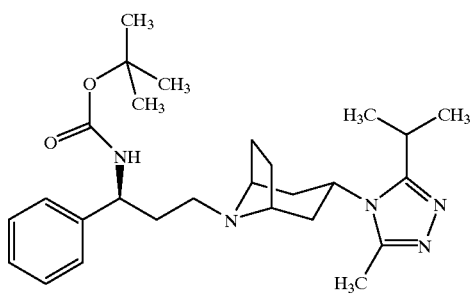

Sodium triacetoxyborohydride (1.7 g, 8.02 mmol) and glacial acetic acid (1 ml, 17.5 mmol) were added to a solution of the title compound from Preparation 9 (1.6 g, 6.84 mmol) and the title compound from Preparation 3 (2 g, 8.03 mmol) in dichloromethane (40 ml) and the reaction stirred at room temperature for 2 hours. The mixture was basified with 10% w/w aqueous potassium carbonate solution and extracted with dichloromethane (2×). The combined organic extracts were washed with brine, dried (MgSO$_4$), filtered and evaporated under reduced pressure. The residue was purified by column chromatography on silica gel using an elution gradient of dichloromethane:methanol: 0.88 ammonia (1:0:0 to 97.5:2.5:0.25, by volume) to afford the title compound as a white foam, 2.5 g $^1$H-NMR (300 MHz, CDCl$_3$): δ [ppm] 1.40 (15H, m), 1.70 (4H, m), 1.80–2.15 (4H, m), 2.30 (2H, m), 2.40 (2H, m), 2.58 (3H, s), 3.00 (1H, m), 3.40 (2H, m) 4.30 (1H, m), 4.85 (1H, m), 6.20 (1H, m), 7.20–7.40 (5H, m).

LRMS: m/z 468.4 (MH$^+$)

Preparation 11
(1S)-3-[3-(3-Isopropyl-5-methyl-4H-1,2,4-triazol-4-yl)-exo-8-azabicyclo[3.2.1]oct-8-yl]-1-phenyl-1-propanamine

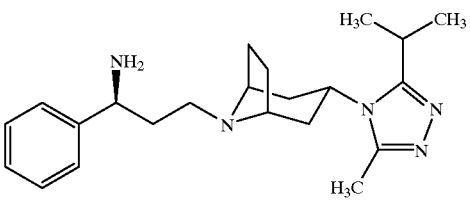

A mixture of the title compound from Preparation 10 (2.5 g, 5.35 mmol), 2.25 M aqueous hydrochloric acid and methanol (70 ml) was heated under reflux for 5 minutes and stirred at room temperature for 1.5 hours. The reaction mixture was allowed to cool to room temperature and evaporated under reduced pressure. The residue was basified by the addition of saturated aqueous sodium carbonate solution (150 ml) and extracted with dichloromethane (2×). The combined organic layers were washed with brine, dried (MgSO$_4$), filtered and evaporated under reduced pressure to afford the title compound as a white foam, 1.80 g.

$^1$H-NMR (400 MHz, CDCl$_3$): δ [ppm] 1.37 (6H, m), 1.42 (4H, m), 1.85 (2H, m), 2.05 (2H, m), 2.20 (2H, m), 2.42 (5H, m), 3.00 (1H, m), 3.37 (2H, m), 4.10 (1H, m), 4.30 (1H, m), 7.30 (5H, m).

$[α]^D$+15.0° (c=0.10, MeOH)

Preparation 12
tert-Butyl (1S)-3-[3-(3-isopropyl-5-methyl-4H-1,2,4-triazol-4-yl)-exo-8-azabicyclo[3.2.1]oct-8-yl-]-1-(3-fluorophenyl)propylcarbamate

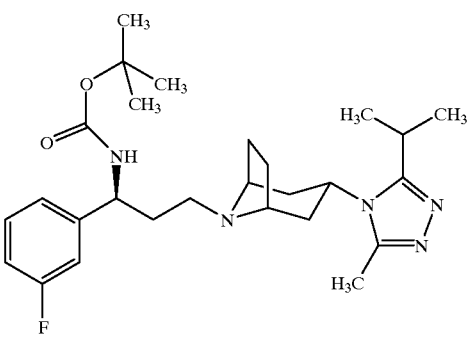

The title compound was prepared from the title compound from Preparation 9 (1.0 g, 4.27 mmol) and tert-butyl (1S)-3-oxo-1-(3-fluorophenyl)propylcarbamate (EP-A-1013276) (2.2 g, 8.23 mmol) using a similar method to that described in Preparation 10, 0.76 g.

LRMS: m/z 486 (MH$^+$).

Preparation 13
(1S)-3-[3-(3-Isopropyl-5-methyl-4H-1,2,4-triazol-4-yl)-exo-8-azabicyclo[3.2.1]oct-8-yl]-1-(3-fluorophenyl)-1-propanamine

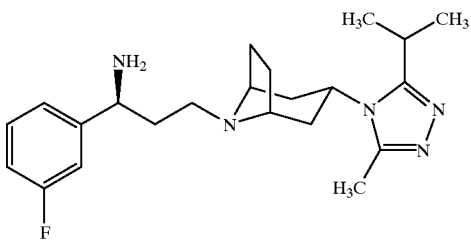

The title compound was prepared from the title compound from Preparation 12 (760 mg, 1.57 mmol) using a similar method to that described in Preparation 11, 200 mg.

LRMS: m/z 386.2 (MH$^+$).

Preparation 14
4,4-Difluorocyclohexanecarbonyl chloride

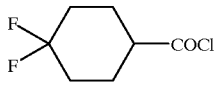

4,4-Difluorocyclohexanecarboxylic acid (118.2 g, 0.72 mol) was dissolved in toluene (296 ml). To the clear solution was added thionyl chloride (261 ml, 3.6 mol) and the resultant solution was heated under reflux for 1.5 hours. A sample was taken and concentrated and $^1$H-NMR indicated complete conversion to the title compound. The reaction was cooled to room temperature and the thionyl chloride was removed under reduced pressure and replaced with toluene to give the title compound as a toluene concentrate at a total volume of 591 ml.

$^1$H-NMR (300 MHz, CDCl$_3$): δ [ppm] 2.29 (1H, m), 2.20–1.70 (8H, m).

Preparation 15
Ethyl (3S)-3-{[(4,4-difluorocyclohexyl)carbonyl]amino}-3-phenylpropanoate

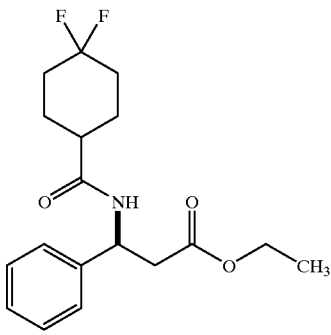

Ethyl (3S)-3-amino-3-phenylpropanoate hydrochloride (10 g, 43.6 mmol) was slurried in dichloromethane (100 ml) and a saturated aqueous solution of sodium carbonate (100 ml) and water (100 ml) added. The mixture was cooled to 0° C. and solution of the title compound from Preparation 14 (7.96 g, 43.6 mmol) in toluene (38 ml) was added to the reaction mixture. The resultant mixture was stirred for 1 hour at room temperature. HPLC analysis of the reaction mixture indicated that the reaction had reached completion. The layers were separated. The pH of the aqueous phase was pH=9. The aqueous layer was washed with dichloromethane (100 ml). The combined organic layers were washed with water (100 ml) and then with 1 M aqueous hydrochloric acid (100 ml) followed by a wash with water (100 ml). The organic layer was concentrated to a brown oil and the oil was granulated in ethyl acetate: heptane 1:2, by volume (50 ml) for 4 hours. The white solid was filtered off and dried in an oven under reduced pressure for 12 hours at 40° C. to yield the title compound as a white solid, 10.9 g, 66% in yield.

$^1$H-NMR (300 MHz, CDCl$_3$): δ [ppm] 7.30 (5H, m), 6.76 (1H, br d), 5.40 (1H, m), 4.08 (2H, q), 2.95–2.75 (2H, m), 2.30–165 (9H, m), 1.15 (3H, t).

LRMS: m/z=338 (M$^-$)

Preparation 16
(1S)-4,4-Difluoro-N-(3-hydroxy-1-phenylpropyl)cyclohexanecarboxamide

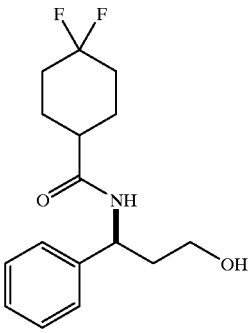

(3S)-3-Amino-3-phenylpropanol (30.9 g, 0.20 mol) was dissolved in dichloromethane (300 ml) and aqueous saturated sodium carbonate solution (300 ml) was added. The resultant biphasic mixture was cooled to 5° C. and the title compound from Preparation 14 was added as a toluene concentrate (37.3 g, 0.20 mol, 224 ml), keeping the temperature below 10° C. The resultant slurry was stirred for 15 minutes at 5° C. HPLC analysis of a sample indicated that the reaction had gone to completion. Water (310 ml) was added and a biphasic mixture was obtained. The layers were separated, the aqueous layer was washed with dichloromethane (300 ml) and the combined organic layers were washed with I M aqueous sodium hydroxide solution (300 ml). The combined organic layers were concentrated under reduced pressure to a brown solid. The solid was slurried in toluene (120 ml) which resulted in a thick white slurry. Methyl-tert-butyl ether (240 ml) was added to give a mobile white slurry. The slurry was stirred at 0° C. for 1 hour and the white solid was filtered off. The solid was dried in an oven under reduced pressure for 12 hours at 40° C. to give the title compound, 53.9 g, 89% yield.

$^1$H-NMR (300 MHz, CDCl$_3$): δ [ppm] 7.30 (5H, m), 6.18 (1H, br d), 5.20 (1H, m), 3.75–3.50 (2H, m), 3.05(1H, br s), 2.18 (4H, m), 2.00–1.62 (7H, m).

LRMS: m/z=297(M$^-$)

Preparation 17
(1S)-4,4-Difluoro-N-(3-oxo-1-phenylpropyl)cyclohexanecarboxamide

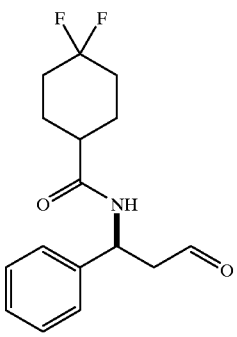

Sulphur trioxide pyridine complex (80.3 g, 0.50 mol) was slurried in dichloromethane (175 ml) under an atmosphere of nitrogen. Dimethylsulfoxide (175 ml) was added and the resultant solution was cooled to 0° C. A solution of the compound from Preparation 16, triethylamine (70 ml, 0.50 mol) and dimethylsulfoxide (88 ml) in dichloromethane (88 ml) was added slowly to the reaction mixture keeping the temperature below 10° C. The resultant yellow solution was stirred at 0° C. for 2 hours until a TLC sample indicated that all starting material was consumed. Water (750 ml) was added and a biphasic mixture was obtained. The mixture was diluted with toluene (750 ml) and the layers were separated. The organic layer was washed with 0.5 M aqueous hydrochloric acid (750 ml) and with brine (750 ml). The organic layer was concentrated under reduced pressure to a brown solid which was taken on to Example 7 without further purification. A sample of the solid was purified by granulation in ethyl acetate: methyl-tert-butyl ether (1:5, 4 ml/g).

$^1$H-NMR (300 MHz, CDCl$_3$): δ [ppm] 9.78(1H, s) 7.30 (5H, m), 6.15 (1H, br-d), 5.50 (1H, m), 3.05 (2H, m), 2.18 (3H, m), 2.00–1.55 (6H, m).
LRMS: m/z=295(M$^-$)

Preparation 18
Benzyl (1S)-3-oxo-1-phenylpropylcarbamate

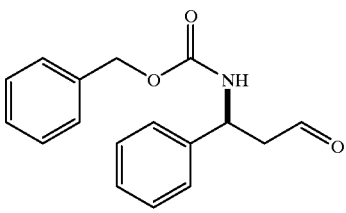

Sulphur trioxide pyridine complex (965 g, 6.1 mol) was slurried in dichloromethane (2 l) under an atmosphere of nitrogen. Dimethylsulfoxide (2 l) was added and the resultant solution was cooled to 0° C. A solution of benzyl (1S)-3-hydroxy-1-phenylpropylcarbamate (577 g, 2.0 mol), triethylamine (845 ml, 6.1 mol) and dimethylsulfoxide (1 l) in dichloromethane (1 ml) was added slowly to the reaction mixture keeping temperature below 10° C. The resultant yellow solution was stirred at 0° C. for 2.5 hours. A sample was analysed by TLC indicating that all starting material was consumed. Water (8.6 l) was added and a biphasic mixture was obtained. The mixture was diluted with toluene (8.6 l) and the layers were separated. The organic layer was concentrated under reduced pressure to yield a brown foam, which was taken on to Preparation 19 without further purification.

$^1$H-NMR (300 MHz, CDCl$_3$): δ [ppm] 9.78(1H, s) 7.30 (5H, m), 6.15 (1H, br-d), 5.50 (1H, m), 3.05 (2H, m), 2.18 (3H, m), 2.00–1.55 (6H, m).
LRMS: m/z 283

Preparation 19
Benzyl (1S)-3-[3-(3-isopropyl-5-methyl-4H-1,2,4-triazol-4-yl)-exo-8-azabicyclo[3.2.1]oct-8-yl]-1-phenylpropylcarbamate

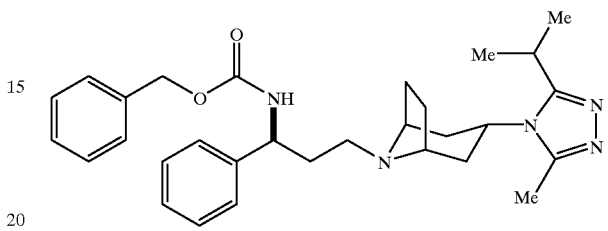

The title compound from Preparation 9 (13.5 g, 32 mmol) was slurried in dichloromethane (27 ml) and a solution of the compound from Preparation 18 (9.93 g, 35 mmol) in toluene (50 ml) and dichloromethane (50 ml) was added to the reaction mixture followed by addition of acetic acid (2.7 ml). To the resultant solution was added sodium triacetoxyborohydride (8.1 g, 38 mmol) in portions. The resultant slurry was stirred at ambient temperature for 1.5 hours. A sample was analysed by HPLC and TLC and the reaction was deemed complete. Water (27 ml) was added followed by 2 M aqueous sodium hydroxide solution (27 ml). The aqueous layer was basified to pH 11–12 by addition of 10 M aqueous sodium hydroxide and the layers were separated. The organic layer was washed with I M aqueous sodium hydroxide (27 ml) and with brine (27 ml). The organic layer was concentrated under reduced pressure to yield a pale brown foam, 13.3 g, 76%.

$^1$H-NMR (300 MHz, CDCl$_3$): δ [ppm] 1.39 (6H, d), 1.55–1.75 (4H, m), 1.84 (2H m), 2.05 (2H, m), 2.15–2.45 (6H, m), 2.97 (1H, m), 3.36 (1H, br-s), 3.45 (1H, br-s), 4.25 (1H, m), 4.93 (1H, br-s) 5.10 (2H, m)7.10–7.40 (10H, m).
LRMS: m/z 502

Preparation 20
(1S)-3-[3-(3-Isopropyl-5-methyl-4H-1,2,4-triazol-4-y)-exo-8-azabicyclo[3.2.1]oct-8-yl]-1-phenyl-1-propanamine

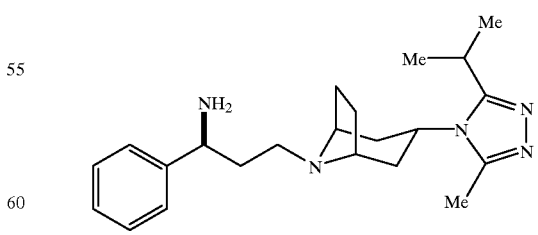

The title compound from Preparation 19 (309 g, 0.62 mol) was dissolved in methanol (3.1 l). Palladium (II) hydroxide (31 g) was added and the resultant slurry was stirred under an atmosphere of hydrogen at 345 kPa (50 psi) for 12 hours.

A sample was taken and analysed by TLC and HPLC and the reaction was deemed complete. The reaction mixture was filtered through Arbocel™ (filtration aid) and the filter pad was washed with methanol (500 ml). The methanolic solution was concentrated to afford the title compound as a white foam, 176 g, 78%. $^1$H-NMR identical to the title compound from Preparation Preparation 21

8-Benzyl-8-azabicyclo[3.2.1]octan-3-one oxime

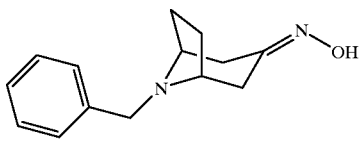

A mixture of the title compound from Preparation 4 (50 g, 0.23 mol) was dissolved in industrial methylated spirit (250 ml). A solution of hydroxylamine hydrochloride (17.8 g, 0.26 mol) in water (250 ml) was added resulting in an exotherm. Sodium bicarbonate (23.4 g, 0.28 mol) was added and a small endotherm and frothing were noted. The resultant solution was stirred for 12 h. A white solid was formed and this was collected by filtration and dried in an oven under reduced pressure for 4 hours at 50° C. to give the title compound as a white solid, 43.1 g, 81% yield.

Preparation 22

Benzyl-8-azabicyclo[3.2.1]octan-3-exo-amine

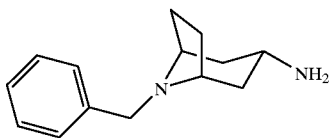

Clean sodium metal (24.3 g, 1.06 mol) was added in pieces to toluene (300 ml) at room temperature and the mixture was heated under reflux. A solution of the title compound from Preparation 5 (20.0 g, 87 mmol) in toluene (200 ml) and pentanol (120 ml) was added slowly over 15 minutes to the refluxing reaction. During this time gas evolution was observed. The resultant mixture was heated under reflux for 2 hours to ensure complete consumption of sodium. A thick white slurry had formed. The reaction was cooled to 80° C. and iso-propyl alcohol (200 ml) was added. The reaction was allowed to cool to room temperature and water (700 ml) was added. The aqueous layer was adjusted to pH 1 by the addition of concentrated hydrochloric acid (140 ml), (exotherm observed). The reaction was stirred for 15 minutes and the layers were separated. Ethyl acetate (700 ml) was added to the aqueous layer which was adjusted to pH 12 by the addition of 10 M aqueous sodium hydroxide (40 ml). The layers were separated and the organic layer was concentrated under reduced pressure to yield a pale yellow oil. Pentanol trapped in the oil was removed by azeotropic distillation with water (200 ml) and the water residue was removed by azeotropic distillation with toluene (200 ml) to give the title compound as a pale yellow oil containing traces of toluene, 18.0 g, 95% yield.

Preparation 23

Exo-N-(8-benzyl-8-azabicyclo[3.2.1]oct-3-yl)-2-methylpropanamide

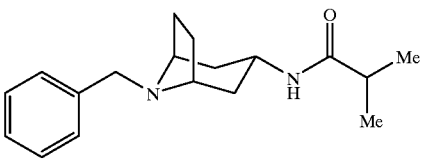

A 20 l fixed rig was charged with dichloromethane (5 l), sodium carbonate (900 g), water (8.7 l) and the title compound from Preparation 6 (1200 g, 5.56 mol). The resultant mixture was cooled to 0° C. Isobutyryl chloride (700 ml, 6.67 mol) was added over 30 minutes keeping temperature below 10° C. The resultant mixture was stirred at from 0° C. to room temperature for 2 hours. The reaction was deemed complete after 2 hours by HPLC analysis. The layers were separated and the aqueous layer was washed with dichloromethane (1.5 l). The aqueous layer was pH 8. The combined organic layers were washed with 1 M aqueous sodium hydroxide solution (1.5 l) and the dichloromethane was distilled off and ethyl acetate added to give a final volume of 3 l. The resultant mixture was heated under reflux to give a clear brown solution. The solution was cooled to 25° C. over 1.5 hours and then to 2° C. over 1 hour and held at that temperature for 30 minutes. The white solid which had formed was separated by filtration and the filtrate was added to the reactor to mobilise the solid stuck on the bottom. The temperature was kept at 2° C. The resultant slurry was added to the filter cake. Ethyl acetate (0.6 l) was added to the reactor to retrieve the remaining solid and the slurry was added to the filter cake. The solid was dried in an oven under reduced pressure to give the title compound, 936 g, 59% yield. The liquors were evaporated under reduced pressure to a total volume of 1.5 l and the resultant brown solution 10 was cooled to 10° C. to give a slurry. The white solid was filtered off and dried in an oven under reduced pressure to give a second crop of title compound, 144 g, 9%. Overall yield: 1080 g, 68%.

Preparation 24

8-Benzyl-3-(3-isopropyl-5-methyl-4H-1,2,4-triazol-4-yl)-exo-8-azabicyclo[3.2.1]octane

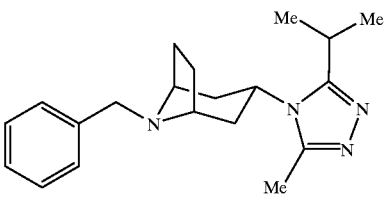

A fixed rig was charged with dichloromethane (7 l) and PCl$_5$ (719 g, 3.45 mol).

The resultant slurry was cooled to 0° C. A solution of the title compound from Preparation 7 (760 g, 2.66 mol) in dichloromethane (2.5 l) was added over 30 minutes keeping the temperature below 10° C. The resultant solution was stirred at from 0° C. to room temperature for 2 hours. The resultant pale yellow solution was cooled to 0° C. A solution of acetic hydrazide (315 g, 4.27 mol) in 2-methyl-2-butanol (ca. 1.5 l) (prepared by dissolving the acetic hydrazide in acetonitrile (1 l) and 2-methyl-2-butanol (2 l) and stripping off the acetonitrile and 500 ml of 2-methyl-2-butanol) was added slowly keeping temperature below 10° C. The resultant solution was stirred at room temperature for 15 hours. The reaction was deemed complete by HPLC analysis after 30 minutes but was held here for convenience. The mixture was cooled to 0° C. and 2 M aqueous sodium hydroxide solution (7.5 l) was added keeping temperature below 20° C. The aqueous layer was adjusted to pH 9 with 10 M aqueous sodium hydroxide solution (ca. 0.5 l). The layers were separated and the aqueous layer was washed with dichloromethane (1 l). The combined organic layers were evaporated under reduced pressure to give a 2-methyl-2-butanol concentrate (ca. 2.5 l). Ethyl acetate (1.5 l) and acetic acid (200 ml) were added. The resultant solution was heated to 80° C. for 30 minutes. The solution was cooled to room temperature overnight. The solution was cooled to 0° C. and the mixture was basified to pH 12 with 2 M aqueous sodium hydroxide solution (2 l). The layers were separated and the aqueous layer was washed with ethyl acetate (1 l). The combined organic layers were concentrated to ca. 2 l under reduced pressure and heptane (2 l) was added and the mixture evaporated to ca. 3 l under reduced pressure. Heptane (1.5 l) and ethyl acetate (300 ml) were added and the mixture was heated under reflux. The solution was cooled to 20° C. for 1 hour and to 0° C. for 2 hours. A white solid formed which was filtered off and dried in an oven under reduced pressure at 40° overnight to give the title compound, 622 g, 72% yield.

Preparation 25
3-(3-Isopropyl-5-methyl-4H-1,2,4-triazol-4-yl)-exo-8-azabicyclo[3.2.1]octane para-toluenesulfonic acid salt

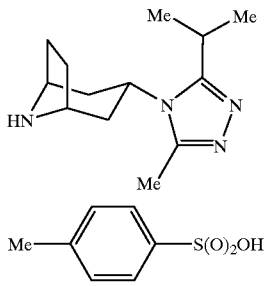

The title compound from Preparation 8 (600 g, 1.85 mol) and para-toluenesulfonic acid monohydrate (351 g, 1.85 mol) were dissolved in methanol (3 l). 10% w/w Palladium-on-carbon (60 g) was added. The mixture was stirred under an atmosphere of hydrogen at 345 kPa (50 psi) and room temperature for 12 hours. A sample was taken and HPLC analysis showed that the reaction was complete. The reaction mixture was filtered through Arbocel™ (filtration aid) and the filter pad was washed with methanol (500 ml). The methanol was evaporated under reduced pressure and the resultant brown oil was dissolved in hot iso-propyl alcohol (1.8 l). The solution was allowed to granulate at room temperature for 12 hours and then at 0° C. for 2 hours. The white solid was filtered off and dried in a vacuum oven for 12 hours to give the title compound, 623 g, 83% yield.

Biological activity

The compounds of Examples 1–5 were tested in the assay for CCR5 binding following the procedures disclosed in Combadiere et al, *J. Leukoc. Biol* 60, 147–52 (1996) (mentioned above). All of the tested compounds were found to have an $IC_{50}$ value of less than 10 nM.

Appendix 1

PXRD Data on the Form A and Form B Polymorphs Isolated From Examples 4 and 6
N-{(1S)-3-[3-(3-Isopropyl-5-methyl-4H-1,2,4-triazol-4-yl)-exo-8-azabicyclo[3.2.1]oct-8-yl]-1-phenylpropyl}4,4-difluorocyclohexanecarboxamide, prepared by the methods of Examples 4 and 6, has been found to exist in 2 polymorphic forms termed Form A and Form B. The PXRD (Powder X-Ray Diffraction) pattern simulation involving d-spacing and relative intensities were calculated from single crystal structures using the Cerius$^2$ Diffraction-Crystal Module. The simulation parameters were:
Wavelength=1.54178 A
Polarisation Factor=0.5
Crystallite Size=500×500×500 Å
Lorentzian Peak Shape The main peaks (in degrees 2-theta) of the simulated PXRD patterns are listed in the following tables.

It will be appreciated by the skilled person that whilst the relative intensities of the various peaks in the tables may vary due to a number of factors including orientation effects of the crystals in the X-ray beam, the purity of the sample being examined or the degree of crystallinity of the sample, the peak positions will remain substantially as defined in the tables.

The skilled person will also appreciate that measurements taken using a different X-ray beam wavelength will result in different shifts in peak position according to the Bragg equation. Such PXRD patterns generated using different wavelengths are considered to be alternative representations of the PXRD patterns of the crystalline materials of the present invention and are thus to be embraced by the scope thereof.

| Angle 2-Theta | Intensity % | Angle 2-Theta | Intensity % | Angle 2-Theta | Intensity % | Angle 2-Theta | Intensity % |
|---|---|---|---|---|---|---|---|
| Peak Listings for Form A | | | | | | | |
| 7.926 | 12.8 | 18.081 | 87.7 | 25.420 | 7.4 | 34.133 | 2.9 |
| 8.350 | 100.0 | 18.410 | 26.1 | 27.152 | 18.7 | 35.210 | 2.8 |
| 9.497 | 18.6 | 18.866 | 24.6 | 27.689 | 13.0 | 35.712 | 2.3 |
| 10.743 | 9.2 | 20.052 | 14.1 | 27.827 | 10.2 | 36.363 | 3.7 |
| 10.852 | 12.6 | 20.368 | 37.9 | 28.492 | 3.2 | 36.584 | 3.3 |
| 11.652 | 20.3 | 20.675 | 7.8 | 28.788 | 5.2 | 37.112 | 6.6 |
| 13.457 | 29.4 | 21.301 | 5.2 | 29.562 | 8.6 | 37.552 | 4.5 |
| 13.705 | 26.7 | 21.998 | 45.4 | 30.018 | 6.6 | 38.777 | 3.8 |
| 14.116 | 25.8 | 22.439 | 57.0 | 30.390 | 9.5 | 40.755 | 4.1 |

-continued

| Angle 2-Theta | Intensity % | Angle 2-Theta | Intensity % | Angle 2-Theta | Intensity % | Angle 2-Theta | Intensity % |
|---|---|---|---|---|---|---|---|
| 14.249 | 50.5 | 22.724 | 12.9 | 30.638 | 6.9 | 41.480 | 4.6 |
| 15.194 | 6.7 | 23.268 | 16.9 | 31.262 | 5.1 | 42.142 | 4.4 |
| 15.959 | 14.5 | 23.718 | 10.2 | 31.454 | 4.6 | 42.916 | 2.7 |
| 16.536 | 33.4 | 23.903 | 8.3 | 32.280 | 5.2 | 43.888 | 4.8 |
| 16.658 | 21.0 | 24.051 | 6.2 | 33.052 | 2.9 | 44.260 | 5.0 |
| 17.125 | 22.7 | 25.003 | 11.2 | 33.315 | 3.6 | 44.779 | 4.8 |
| 17.637 | 36.9 | 25.280 | 7.0 | 33.680 | 4.2 | | |
| Peak Listings for Form B | | | | | | | |
| 7.622 | 1.4 | 20.712 | 13.1 | 29.009 | 9.6 | 36.634 | 8.0 |
| 9.561 | 5.0 | 21.697 | 8.5 | 29.588 | 3.2 | 36.986 | 4.0 |
| 9.992 | 43.3 | 22.406 | 23.8 | 30.137 | 6.6 | 37.635 | 2.9 |
| 11.194 | 47.6 | 23.037 | 27.3 | 30.373 | 6.3 | 38.255 | 4.5 |
| 11.528 | 24.0 | 23.138 | 27.5 | 30.726 | 9.2 | 38.442 | 4.8 |
| 12.619 | 47.9 | 23.826 | 4.4 | 31.338 | 8.9 | 39.064 | 5.1 |
| 14.156 | 44.8 | 23.983 | 4.1 | 31.824 | 14.2 | 39.391 | 3.4 |
| 15.052 | 51.2 | 24.484 | 5.3 | 32.351 | 4.5 | 39.792 | 3.9 |
| 15.28 | 27.0 | 24.691 | 6.4 | 33.105 | 2.4 | 40.540 | 2.1 |
| 16.041 | 64.8 | 25.181 | 10.3 | 33.470 | 2.5 | 40.985 | 6.5 |
| 16.371 | 40.6 | 25.358 | 8.7 | 33.685 | 2.5 | 42.126 | 3.7 |
| 17.070 | 36.1 | 25.928 | 10.6 | 34.032 | 6.7 | 42.397 | 4.3 |
| 17.360 | 78.0 | 26.390 | 7.2 | 34.447 | 2.5 | 42.983 | 2.5 |
| 18.046 | 66.6 | 26.696 | 13.2 | 35.131 | 9.0 | 43.328 | 3.4 |
| 18.946 | 23.9 | 27.301 | 3.5 | 35.643 | 3.9 | 44.219 | 3.6 |
| 19.202 | 16.1 | 27.864 | 5.1 | 35.812 | 4.0 | 44.690 | 5.5 |
| 20.088 | 100.0 | 28.498 | 10.8 | 36.239 | 4.0 | | |

What is claimed is:

1. A compound of the formula:

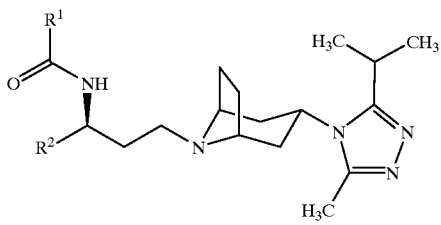

I or a pharmaceutically acceptable salt or solvate thereof, wherein:

$R^1$ is $C_{3-6}$ cycloalkyl optionally substituted by one or more fluorine atoms, or $C_{1-6}$ alkyl optionally substituted by one or more fluorine atoms, or $C_{3-6}$ cycloalkylmethyl optionally ring-substituted by one or more fluorine atoms; and $R^2$ is phenyl optionally substituted by one or more fluorine atoms.

2. The compound of claim 1 of the formula:

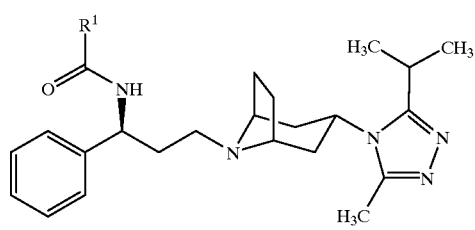

IA or a pharmaceutically acceptable salt or solvate thereof, wherein:

$R^1$ is either $C_{3-4}$ cycloalkyl optionally substituted by one or more fluorine atoms, or $C_{1-6}$ alkyl optionally substituted by one or more fluorine atoms.

3. The compound of claim 1, wherein $R^1$ is either $C_{4-6}$ cycloalkyl optionally substituted by one or two fluorine atoms, or $C_{1-4}$ alkyl optionally substituted by from one to three fluorine atoms.

4. The compound of claim 3, wherein $R^1$ is either cyclobutyl, cyclopentyl, 4,4-difluorocyclohexyl or 3,3,3-trifluoropropyl.

5. The compound of claim 1, wherein $R^2$ is phenyl optionally substituted by 1 or 2 fluorine atoms.

6. The compound of claim 5, wherein $R^2$ is phenyl or monofluorophenyl.

7. The compound of claim 6, wherein $R^2$ is phenyl or 3-fluorophenyl.

8. The compound of claim 1 which is selected from the group consisting of:

N-{(1S)-3-[3-(3-Isopropyl-5-methyl-4H-1,2,4-triazol-4-yl)-exo-8-azabicyclo[3.2.1]oct-8-yl]-1-phenylpropyl}cyclobutanecarboxamide;

N-{(1S)-3-[3-(3-Isopropyl-5-methyl-4H-1,2,4-triazol-4-yl)-exo-8-azabicyclo[3.2.1]oct-8-yl]-1-phenylpropyl}cyclopentanecarboxamide;

N-{(1S)-3-[3-(3-Isopropyl-5-methyl-4H-1,2,4-triazol-4-yl)-exo-8-azabicyclo[3.2.1]oct-8-yl]-1-phenylpropyl}-4,4,4-trifluorobutanamide;

N-{(1S)-3-[3-(3-Isopropyl-5-methyl-4H-1,2,4-triazol-4-yl)-exo-8-azabicyclo[3.2.1]oct-8-yl]-1-phenylpropyl}-4,4-difluorocyclohexanecarboxamide; and N-{(1S)-3-[3-(3-Isopropyl-5-methyl-4H-1,2,4-triazol-4-yl)-exo-8-azabicyclo[3.2.1]oct-8-yl]-1-(3-fluorophenyl)propyl}-4,4-difluorocyclohexanecarboxamide;

or a pharmaceutically acceptable salt or solvate of any thereof.

9. A pharmaceutical composition comprising a compound of claim 1 and one of a pharmaceutically acceptable excipient, a pharmaceutically acceptable diluent or a pharmaceutically acceptable carrier.

10. A method of antagonizing a CCR5 receptor in a mammal comprising administering to said mammal in need thereof an effective amount of a compound of claim 1 to antagonize the CCR5 receptor-associated responses in said mammal.

11. A method of treating an inflammatory disease in a mammal comprising administering to said mammal an effective amount of a compound of claim 1.

12. A compound of the formula:

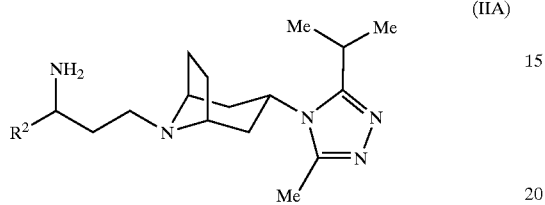
(IIA)

wherein $R^2$ is phenyl optionally substituted by one or more fluorine atoms.

13. The compound of claim 12, wherein $R^2$ is phenyl.

14. The compound of claim 12 of the formula:

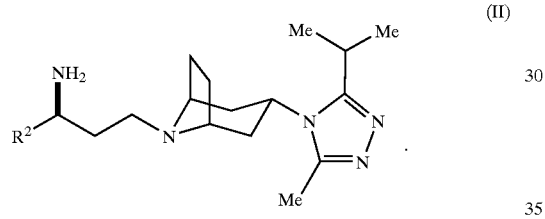
(II)

15. The compound of claim 14, wherein $R^2$ is phenyl.

16. A compound of the formula:

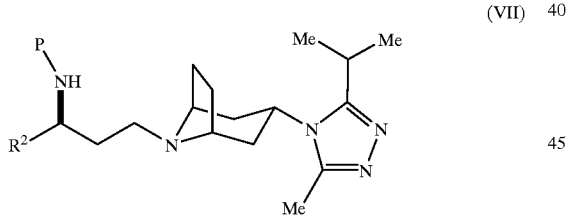
(VII)

wherein $R^2$ is phenyl optionally substituted by one or more fluorine atoms; and P is a protecting group.

17. The compound of claim 16, wherein $R^2$ is phenyl.

18. The compound of claim 16, wherein P is t-butyloxycarbonyl or benzyloxycarbonyl.

19. A compound of the formula:

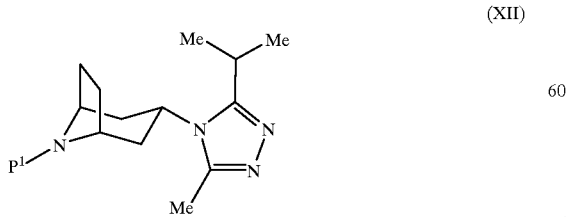
(XII)

wherein $P^1$ is hydrogen or a protecting group.

20. The compound of claim 19, wherein $P^1$ is benzyl.

21. The compound of claim 19, or a salt thereof, having the formula:

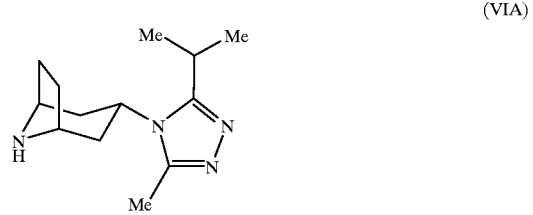
(VIA)

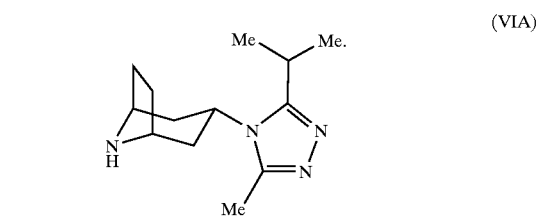
(VIA)

22. The p-toluenesulphonate salt of the compound of claim 21.

23. A compound of the formula:

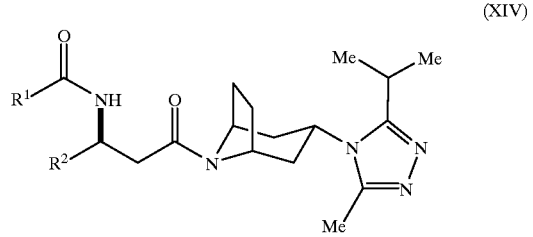
(XIV)

wherein $R^1$ is $C_{3-6}$ cycloalkyl optionally substituted by one or more fluorine atoms, or $C_{1-6}$ alkyl optionally substituted by one or more fluorine atoms, or $C_{3-6}$ cycloalkylmethyl optionally ring-substituted by one or more fluorine atoms; and $R^2$ is phenyl optionally substituted by one or more fluorine atoms.

24. The compound of claim 23, wherein $R^2$ is phenyl.

25. A compound of the formula:

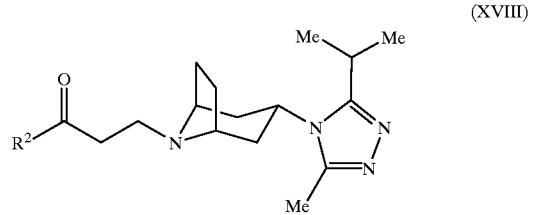
(XVIII)

where $R^2$ is phenyl optionally substituted by one or more fluorine atoms.

26. The compound of claim 25, wherein $R^2$ is phenyl.

27. A compound of the formula:

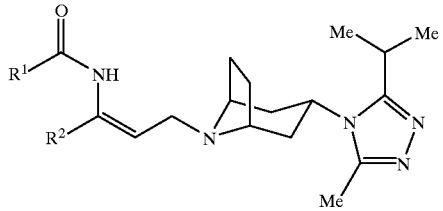
(XIX)

wherein $R^1$ is $C_{3-6}$ cycloalkyl optionally substituted by one or more fluorine atoms, or $C_{1-6}$ alkyl optionally substituted by one or more fluorine atoms, or $C_{3-6}$ cycloalkylmethyl optionally ring-substituted by one or more fluorine atoms; and $R^2$ is phenyl optionally substituted by one or more fluorine atoms.

28. The compound of claim 27, wherein $R^2$ is phenyl.

29. A compound selected from the group consisting of:

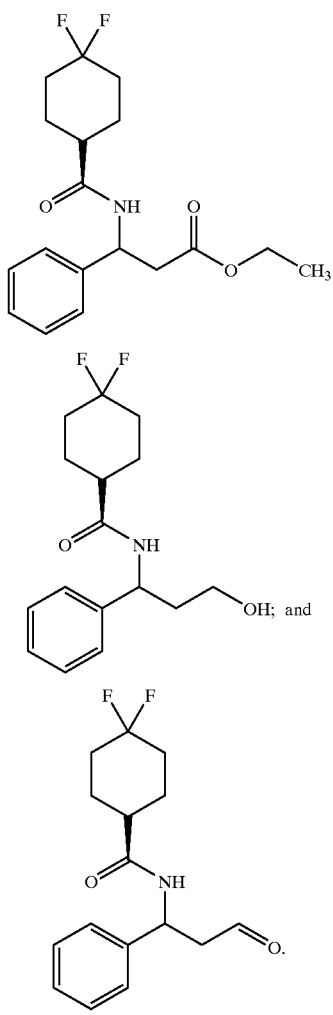

30. A process for the preparation of a compound of claim 1 selected from a process which comprises:

(a) coupling a compound of the formula:

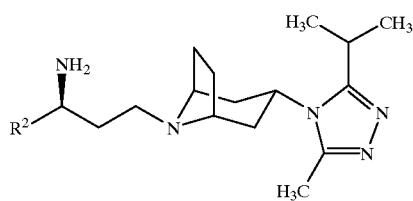
II with a compound of formula:

$R^1CO_2H$ (III);

or (b) reaction of a compound of the formula (II) with a compound of the formula:

$R^1COZ$ (VIB)

where Z is a carboxylic acid activating, group; or (c) reduction of a compound of the formula:

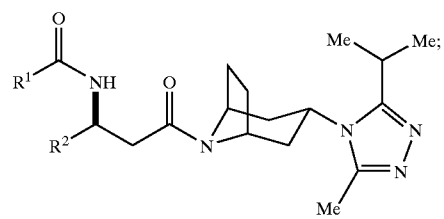
(XIV)

(d) reductive amination using a compound of the formula:

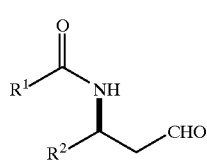
(XVI)

and a compound of the formula:

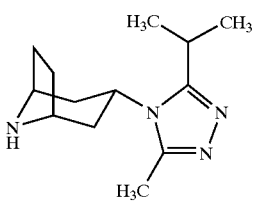
(VIA)

or a salt thereof; or (e) reductive amination using a compound of the formula:

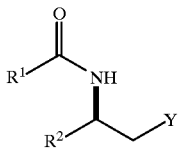
(XV)

where Y is CN, and a compound of the formula (VIA), or a salt thereof; or (f) alkylation of a compound of the formula (VIA), or a salt thereof, with a compound of the formula:

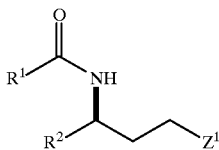
(XVII)

where $Z^1$ is a leaving group; or (g) asymmetric reduction of a compound of the formula:

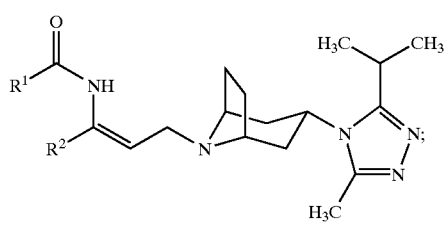
(XIX)

or (h) reaction of a compound of the formula (II), or a metal salt thereof, with a compound of the formula:

$R^1CO_2R^5$ (XXIV)

where $R^5$ is an ester forming group; or (i) reaction of a compound of the formula:

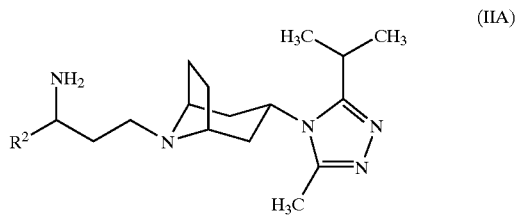
(IIA)

either with a compound of the formula (III) under coupling conditions, or a compound of the formula (VIB), and in the presence of a a chiral catalyst:

wherein any one of processes (a) through (i) is optionally followed by conversion of a compound of claim 1 a pharmaceutically acceptable salt thereof.

31. A compound of claim 1 which is
N-{(1S)-3-[3-(3-Isopropyl-5-methyl-4H-1,2,4-triazol-4-yl)-exo-8-azabicyclo[3.2.1]oct-8-yl]-1-phenylpropyl}cyclobutanecarboxamide or a pharmaceutically acceptable salt or solvate thereof.

32. A compound of claim 1 which is
N-{(1S)-3-[3-(3-Isopropyl-3-methyl-4H-1,2,4-triazol-4-yl)-exo-8-azabicyclo[3.2.1]oct-8-yl]-1-phenylpropyl}cyclopentanecarboxamide or a pharmaceutically acceptable salt or solvate thereof.

33. A compound of claim 1 which is
N-{(1S)-3-[3-(3-Isopropyl-5-methyl-4H-1,2,4-triazol-4-yl)-exo-8-azabicyclo[3.2.1]oct-8-yl]-1-phenylpropyl}-4,4,4-trifluorobutanamide or a pharmaceutically acceptable salt or solvate thereof.

34. A compound of claim 1 which is N-{(1S)-3-[3-(3-Isopropyl-5-methyl-4H-1,2,4-triazol-4-yl)-exo-8-azabicyclo[3.2.1]oct-8-yl]-1-phenylpropyl}-4,4-difluorocyclohexanecarboxamide or a pharmaceutically acceptable salt or solvate thereof.

35. A compound of claim 1 which is
N-{(1S)-3-[3-(3-Isopropyl-5-methyl-4H-1,2,4-triazol-4-yl)-exo-8-azabicyclo[3.2.1]oct-8-yl]-1-(3-fluorophenyl)propyl}-4,4-difluorocyclohexanecarboxamide or a pharmaceutically acceptable salt or solvate thereof.

* * * * *